United States Patent
Weinstock-Rosin

(10) Patent No.: US 9,867,798 B2
(45) Date of Patent: Jan. 16, 2018

(54) LADOSTIGIL THERAPY FOR IMMUNOMODULATION

(71) Applicant: Yissum Research Development Company of the Hebrew University of Jerusalem Ltd., Jerusalem (IL)

(72) Inventor: Marta Weinstock-Rosin, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 14/453,187

(22) Filed: Aug. 6, 2014

(65) Prior Publication Data
US 2014/0349927 A1 Nov. 27, 2014

Related U.S. Application Data

(63) Continuation of application No. PCT/IL2013/050124, filed on Feb. 11, 2013.

(60) Provisional application No. 61/597,794, filed on Feb. 12, 2012.

(51) Int. Cl.
| A61K 38/28 | (2006.01) |
| A61K 31/27 | (2006.01) |
| A61K 45/06 | (2006.01) |
| A61K 31/325 | (2006.01) |

(52) U.S. Cl.
CPC ............ *A61K 31/27* (2013.01); *A61K 31/325* (2013.01); *A61K 45/06* (2013.01)

(58) Field of Classification Search
None
See application file for complete search history.

(56) References Cited

U.S. PATENT DOCUMENTS

| 6,251,938 | B1 | 6/2001 | Chorev et al. | |
| 6,303,650 | B1 * | 10/2001 | Chorev | C07C 271/24 514/480 |
| 6,462,222 | B1 * | 10/2002 | Chorev | C07C 271/24 560/134 |
| 6,538,025 | B2 | 3/2003 | Chorev et al. | |
| 7,335,685 | B2 | 2/2008 | Bahar | |
| 7,375,249 | B2 | 5/2008 | Boulton et al. | |
| 7,476,757 | B2 | 1/2009 | Boulton et al. | |
| 7,491,847 | B2 | 2/2009 | Frenkel et al. | |
| 2005/0222123 | A1 | 10/2005 | Tracey et al. | |
| 2006/0189685 | A1 | 8/2006 | Licht et al. | |
| 2006/0189819 | A1 | 8/2006 | Bahar | |
| 2006/0199974 | A1 | 9/2006 | Boulton et al. | |
| 2007/0078172 | A1 * | 4/2007 | McElroy | A61K 31/00 514/355 |
| 2007/0088082 | A1 | 4/2007 | Aronhime et al. | |
| 2007/0093549 | A1 | 4/2007 | Aronhime et al. | |
| 2007/0112217 | A1 | 5/2007 | Frenkel et al. | |
| 2007/0135518 | A1 | 6/2007 | Weinstock-Rosin et al. | |
| 2007/0203232 | A1 | 8/2007 | Piryatinsky | |
| 2007/0232691 | A1 | 10/2007 | Goren et al. | |
| 2007/0293583 | A1 | 12/2007 | Weinstock-Rosin et al. | |
| 2008/0187944 | A1 * | 8/2008 | Allam | C12Q 1/46 435/20 |
| 2009/0081314 | A1 * | 3/2009 | Wills | A61K 31/445 424/643 |

FOREIGN PATENT DOCUMENTS

| WO | 9827055 A1 | 6/1998 |
| WO | 2005051371 A1 | 6/2005 |
| WO | 2006130726 A2 | 12/2006 |
| WO | 2007087029 A2 | 8/2007 |
| WO | 2009022345 A1 | 2/2009 |
| WO | 2009022346 A2 | 2/2009 |
| WO | 2012059920 A1 | 5/2012 |

OTHER PUBLICATIONS

Suzuki S, Tanaka K, Suzuki N. Ambivalent aspects of interleukin-6 in cerebral ischemia: inflammatory versus neurotrophic aspects. J Cereb Blood Flow Metab. Mar. 2009;29(3):464-79 Epub Nov. 19, 2008.*
Kukielka GL, Smith CW, Manning AM, Youker KA, Michael LH, Entman ML. Induction of interleukin-6 synthesis in the myocardium. Potential role in postreperfusion inflammatory injury. Circulation. Oct. 1, 1995;92(7):1866-75.*
Di Paola R, Melani A, Esposito E, Mazzon E, Paterniti I, Bramanti P, Pedata F, Cuzzocrea S. Adenosine A2A receptor-selective stimulation reduces signaling pathways involved in the development of intestine ischemia and reperfusion injury. Shock. May 2010;33(5):541-51.*
Karampetsou MP, Liossis SN, Sfikakis PP. TNF-α antagonists beyond approved indications: stories of success and prospects for the future. QJM. Dec. 2010;103(12):917-28.*
Ito H. IL-6 and Crohn's disease. Curr Drug Targets Inflamm Allergy. Jun. 2003;2(2):125-30.*
Ursini F, Naty S, Grembiale RD. Infliximab and insulin resistance. Autoimmun Rev. Jun. 2010;9(8):536-9.*
Iliodromitis EK, Lazou A, Kremastinos DT. Ischemic preconditioning: protection against myocardial necrosis and apoptosis. Vasc Health Risk Manag. 2007;3(5):629-37.*
Holmes et al (Neurology 73:768-774, 2009).*
Yaffe et al (JAMA 292:2237-2242, 2004).*
Appa et al (Lipids in Health and Disease 4:28 (2006).*
Yogev-Falach et al (FASEB J 20:2177-2179, 2017).*
Borovikova et al., (2000) Vagus nerve stimulation attenuates the systemic inflammatory response to endotoxin. Nature 405(6785): 458-62.
Cytokines link Toll-like receptor 4 signaling to cardiac dysfunction after global myocardial ischemia.

(Continued)

*Primary Examiner* — Craig Ricci
(74) *Attorney, Agent, or Firm* — Vorys, Sater, Seymour & Pease LLP

(57) ABSTRACT

Methods for treating individuals suffering from inflammation, specifically systemic inflammation including septic shock and inflammatory conditions affecting the gastrointestinal, myocardial and endocrine systems with ladostigil.

4 Claims, 3 Drawing Sheets

(56) References Cited

OTHER PUBLICATIONS

Fassbender et al., (2000) Alzheimer's disease: an inflammatory disease? Neurobiol Aging 21(3): 433-436.

Gross et al., (2007) Pharmacologic therapeutics for cardiac reperfusion injury. Expert Opin Emerg Drugs 12(3): 367-388.

Holmes (2012) Review: systemic inflammation and Alzheimer's disease. Neuropathol Appl Neurobiol 39(1): 51-68.

Holmes et al., (2009) Systemic inflammation and disease progression in Alzheimer disease. Neurology 73(10): 768-74.

Langley et al., (2004) Central but not the peripheral action of cholinergic compounds suppresses the immune system. J Neuroimmunol 148(1-2): 140-5.

Merlo et al., (2010) Alzheimer's disease: brain expression of a metabolic disorder? Trends Endocrinol Metab 21(9): 537-544.

Nakano et al., (2000) Ischemic preconditioning: from basic mechanisms to clinical applications. Pharmacol Ther 86(3): 263-75.

Nizri et al., (2005) Bifunctional compounds eliciting both anti-inflammatory and cholinergic activity as potential drugs for neuroinflammatory impairments. Neurosci Lett 376(1): 46-50.

Nizri et al., (2006) Anti-inflammatory properties of cholinergic up-regulation: A new role for acetylcholinesterase inhibitors. Neuropharmacology 50(5): 540-7.

Nizri et al., (2007) IBU-octyl-cytisine, a novel bifunctional compound eliciting anti-inflammatory and cholinergic activity, ameliorates CNS inflammation by inhibition of T-cell activity. Int Immunopharmacol 7(9): 1129-39.

Panarsky et al., (2010) Anti-inflammatory properties of ladostigil and its metabolites in primary microglia. Alzheimer's & Dementia: The Journal of the Alzheimer's Association 6(4): S557-S558.

Panarsky et al., (2012) Anti-inflammatory effects of ladostigil and its metabolites in aged rat brain and in microglial cells. J Neuroimmune Pharmacol 7(2): 488-98.

Przyklenk (2011) Efficacy of cardioprotective 'conditioning' strategies in aging and diabetic cohorts: the co-morbidity conundrum. Drugs Aging 28(5): 331-43.

Reale et al., (2004) Treatment with an acetylcholinesterase inhibitor in Alzheimer patients modulates the expression and production of the pro-inflammatory and anti-inflammatory cytokines. J Neuroimmunol 148(1-2): 162-71.

Sandborn et al., (1997) Transdermal nicotine for mildly to moderately active ulcerative colitis. A randomized, double-blind, placebo-controlled trial. Ann Intern Med 126(5): 364-71.

Tyagi et al., (2007) Effect of anti-dementia drugs on LPS induced neuroinflammation in mice. Life Sci 80(21): 1977-83.

Wang et al., (2004) Cholinergic agonists inhibit HMGB1 release and improve survival in experimental sepsis. Nat Med 10(11): 1216-21.

Weinstock et al., (2000) Development of a novel neuroprotective drug (TV3326) for the treatment of Alzheimer's disease, with cholinesterase and monoamine oxidase inhibitory activities. Drug Development Research 50(3-4): 216-222.

Wellen and Hotamisligil (2005) Inflammation, stress, and diabetes. J Clin Invest 115(5): 1111-9.

* cited by examiner

LADOSTIGIL THERAPY FOR IMMUNOMODULATION

FIELD OF THE INVENTION

The invention relates to pharmaceutical compositions and dosage units comprising ladostigil and methods of using the same for inhibiting inflammation.

BACKGROUND OF THE INVENTION

Inflammation is a biological response to injury, infection or irritation in which a cascade of cellular and microvascular reactions serves to eradicate the infection, remove damaged tissue and generate new tissue. Immune responses mediated by various immune effectors and mediators initiate and tightly regulate the inflammatory response. However, while the normal immune system is closely regulated, aberrations in immune responses are not uncommon. Such dysregulated or excessive inflammatory reactions may result in potentially harmful processes, leading in turn to organ damage and various pathologies due to excessive exposure to inflammatory mediators or cellular effectors. These include acute pathologies such as septic shock, and chronic pathologies such as chronic gastrointestinal inflammatory diseases and autoimmune diseases.

Immune responses within the brain are specialized and differ considerably from those in the periphery. Such differences endow the central nervous system (CNS) with an immune-privilege status. Thus, the CNS is relatively secluded from the peripheral immune system, and has its own residential immune network, in which glial cells (mainly microglia and astrocytes) not only serve supportive and nutritive roles for neurons, but also defend the CNS from stress and pathogenic insults by transiently up-regulating inflammatory processes. In contrast, systemic inflammatory reactions are mediated by the peripheral immune system, and involve different leukocyte subsets, including blood borne monocytes, tissue resident macrophages, and specialized lymphocytes.

Gastrointestinal Inflammation

Crohn's disease, ulcerative colitis, inflammatory bowel disease and other related conditions form a spectrum of chronic inflammatory diseases of the gastrointestinal tract. Inflammatory bowel disease (IBD), a form of chronic gastrointestinal inflammation, includes a group of chronic inflammatory disorders including ulcerative colitis (UC) and Crohn's disease (CD). These diseases appear to result from the unrestrained activation of an inflammatory response in the intestines. This inflammatory cascade is thought to be perpetuated through the actions of pro-inflammatory cytokines and selective activation of lymphocyte subsets. In patients with IBD, ulcers and inflammation of the inner lining of the intestines lead to symptoms of abdominal pain, diarrhea, and rectal bleeding. Ulcerative colitis occurs in the large intestine, while in Crohn's the disease can involve the entire GI tract, both small and large intestines. UC is a condition that primarily affects the superficial layer of the colon mucosa and histological analyses reveal ulceration of the mucosa, blunting and loss of crypts, and an inflammatory infiltrate.

Treatment of IBD commonly utilizes a variety of orally administered systemic anti-inflammatory agents designed to reduce the inflammatory response. First line therapy commonly employs 5-aminosalicylate (Mesalamine) or its precursors, immunosuppressive agents such as cyclosporine, corticosteroids such as beclometasone and biologics such as infliximab (chimeric monoclonal antibody to tumor necrosis factor α, TNFα), anti-leukocyte adhesions molecules, and daclizumab (a recombinant humanized immunoglobulin G1 monoclonal antibody to interleukin-2 receptor α, IL-2Rα). Due to the postulated role of bacterial infection in IBD, eradication of the gut bacterial flora is also attempted by means that include use of antibiotics and antimicrobial agents. About 20-25% of the patients with UC fail to respond to medical therapy and therefore are referred to surgery for total proctocolectomy. In general, patients with CD are less responsive to medical therapy and usually do not respond to surgical treatment.

Diabetes

Diabetes mellitus is a common metabolic disorder associated with abnormally high levels of glucose in the blood. There are two major types of diabetes mellitus, termed type 1 and type 2.

Type 1 Diabetes (T1 D, or Insulin Dependent Diabetes Mellitus, IDDM) is caused by a deficiency of insulin due to an autoimmune response which leads to the destruction of the beta cells in the Islets of Langerhans of the pancreas. An initial phase of type 1 diabetes includes an inflammation of the pancreatic islets, known as insulitis. Insulitis is characterized by leukocyte and macrophage infiltration into the islets followed by the actual destruction of pancreatic beta cells in an autoimmune attack. Studies show that IDDM progresses as a predominant inflammatory beta-cell dysfunction without actual beta-cell destruction until late in the disease process.

Type 2 Diabetes (T2D, formerly non-insulin-dependent diabetes mellitus, NIDDM, or adult-onset diabetes) appears to result from both a strong genetic predisposition, and environmental factors such as diet, physical activity, and age. It is a metabolic disorder that is characterized by high blood glucose in the context of relative insulin resistance and insulin deficiency. Type 2 diabetes is caused by a combination of insulin resistance and diminished beta cell function. Insulin resistance is defined as the lack of sensitivity to insulin in adipose skeletal muscle, and hepatic tissue. As a result, the pancreas produces larger than normal amounts of insulin, a state defined as hyperinsulinemia. However, eventually the pancreas fails and insulin secretion levels decrease.

Increased levels of pro-inflammatory cytokines TNF-α, IL-1β and IL-6, are also found in the blood of diabetic patients. Inflammation may be secondary to oxidative stress induced by hyperglycemia, together with products of glycation and lipid peroxidation. A primary factor contributing to the development of insulin resistance and T2D is obesity which is characterized by a state of low-grade inflammation, in which proliferating white blood cells and activated macrophages migrate from the circulation to the tissues (Wellen et al. 2005).

Unfortunately, currently there are no cures for diabetes. Prescribed treatment generally involves control of hyperglycemia to relieve symptoms and prevent complications while minimizing hypoglycemic episodes.

Myocardial Ischemia

Heart diseases due to myocardial ischemia or ischemic heart failure are major causes of death in developed countries. When hearts are exposed to ischemia, absence of a supply of oxygen leads to the depletion of intra myocardial ATP, which if decreased by 90%, causes irreversible structural changes in the myocardium. On re-oxygenation, recovery of aerobic metabolism results in an overload of reactive oxygen species (ROS), superoxide and hydroxyl radicals which can damage cellular structures, enzymes, or channel proteins on the cellular membrane. These events can trigger the activation of inflammatory cascades and release of cytokines (Cha et al., 2008) which make cells more susceptible to myocardial contractile dysfunction or death.

Treatment for myocardial ischemia is directed at improving blood flow to the heart muscle and may include medications, a procedure to open blocked arteries or coronary artery bypass surgery. However, surgical interventions and in particular cardiac and vascular interventions possess a further risk for perioperative myocardial ischemic damage. One method for minimizing perioperative damage is known as myocardial ischemic preconditioning (IPC).

IPC is a well-established procedure for protection of the heart, especially in patients undergoing cardiac surgery. IPC consists of short ischemic period/s separated by short (re)perfusions, applied to the heart prior to prolonged ischemic insult. In humans and animal models, IPC protects the heart against injury associated with ischemia, and reduces the consequent ventricular dysfunction (Nakano et al., 2000).

Morbidity and mortality due to ischemic cardiovascular diseases are significantly higher in the elderly than in young adults. Aging causes changes in structural components of the myocardium, impairs mitochondrial function, increases monoamine oxidase (MAO)-A, and the generation of reactive oxygen species (ROS). However, hearts from aged subjects and hearts of diabetic patients are generally resistant to cardio-protection from preconditioning procedures (Przyklenk, 2011). Thus, there remains an unmet need for protecting aged subjects from myocardial damage particularly induced by cardiovascular surgery.

Endotoxin and Associated Responses

Endotoxin is invariably associated with Gram-negative bacteria. Although the term "endotoxin" is occasionally used to refer to any cell-associated bacterial toxin, in bacteriology it is properly reserved to refer to the lipopolysaccharide (LPS) complex associated with the outer membrane of Gram-negative pathogens such as *Escherichia coli, Salmonella, Shigella, Pseudomonas, Neisseria, Haemophilus influenzae, Bordetella pertussis* and *Vibrio cholerae.*

The biological activity of endotoxin is associated with the lipopolysaccharide (LPS). Toxicity is associated with the lipid component (Lipid A) and immunogenicity is associated with the polysaccharide components. The cell wall antigens (O antigens) of Gram-negative bacteria are components of LPS. LPS elicits a variety of inflammatory responses in animals and it activates complement by the alternative (properdin) pathway.

Specifically, LPS induces a variety of acute inflammatory responses which are qualitatively similar to those that occur during the early stages of septic shock. Moreover, LPS induces the release of a wide variety of inflammatory mediators such as pro-inflammatory cytokines (e.g. tumor necrosis factor-alpha, IL-1 beta, IL-6, IL-8), activation of the fibrinolytic system, kallikrein-kinin generation and phospholipase A2 release. Phagocytic leukocytes are primed for enhanced inflammatory responses following endotoxin administration.

Acetylcholine Esterase (AChE) Inhibitors

Acetylcholine esterase (AChE) inhibitors are a family of compounds that inhibit the breakdown of acetylcholine by the enzyme AChE, thereby increasing both the level and duration of action of the neurotransmitter acetylcholine. Reversible, AChE inhibitors Tacrine and Donepezil or pseudo-reversible AChE inhibitors such as Rivastigmine and Physostigmine, are indicated for the alleviation of neurological disorders associated with impaired acetylcholine levels, such as Alzheimer's disease (AD).

Since certain immune system cells possess various subtypes of muscarinic and nicotinic cholinergic receptors and/or synthesize AChE, it was suggested that cholinergic up-regulation may result in anti-inflammatory effects. Indeed, certain preclinical tests with acetylcholine or its agonists such as nicotine suggested immunomodulation following cholinergic up regulation (see, e.g. Borovikova et al., 2000, Wang et al., 2004). In addition, the use of nicotine patches for the treatment of human ulcerative colitis was examined in clinical trials (Sandborn et al., 1997). However, the use of nicotine as a therapeutic agent, particularly for oral use, is limited by its toxicity.

In addition, certain AChE inhibitors such as donepezil, tacrine and rivastigmine were shown to affect the immune system, particularly in the CNS. This activity was largely shown to depend on AChE inhibition and/or require their presence in the CNS. See, e.g. Nizri et al. (2006), Reale et al. (2004), Tyagi et al. (2007) and Langley et al. (2004). U.S. Patent Application Publication No. 2005/0222123 is directed to a method of treating a subject with a cytokine-mediated inflammatory disorder comprising administering to the subject a cholinesterase inhibitor other than galantamine. WO 2009/022345 to some of the inventors of the present invention is directed to the use of rivastigmine and related phenyl carbamates for the treatment of multiple sclerosis. WO 2009/022346 to some of the inventors of the present invention relates to the use of rivastigmine and such related phenyl carbamates for treating inflammatory bowel disease and other autoimmune and chronic inflammatory gastrointestinal diseases and conditions.

However, other reports indicated that the immunomodulatory effects exerted by AChE inhibitors were not sufficient to alleviate the disease outcome, particularly outside the CNS. For example, Nizri et al. (2005) discloses bi-functional compounds consisting of the non-steroidal anti-inflammatory drug ibuprofen and pyridostigmine, found effective in an EAE mouse model. Although treatment of mice by pyridostigmine alone resulted in reduced lymphocyte proliferation, such treatment did not change disease severity. Another such bi-functional compound, namely IBU-Octyl-Cytisine, containing ibuprofen and Cytisine as the nicotinic agonist, has been described by Nizri et al. (2007), which further report that each moiety separately failed to reproduce the effect of this compound. Holmes et al. (2009) found that high levels of serum TNF-α, which were associated with the degree of baseline cognitive impairment in AD patients, was independent of concomitant cholinesterase use.

One problem associated with the use of AChE inhibitors is the high degree of side effects which develop upon oral administration. These side effects include nausea, vomiting, gastrointestinal discomfort and diarrhea. Minimizing these side effects simply by limiting the administered dose may not always be applicable, because the efficacy of the drug for which AChE inhibitory activity is necessary may be impaired at lower doses.

In addition, many AChE inhibitors are contraindicated in treatment of patients afflicted with non-neurological pathologies, due to adverse effects. For example, rivastigmine is contraindicated in diabetic patients as it can increase blood sugar and promotes loss of diabetic control. Other patient populations in which rivastigmine treatment is contraindicated are those with cardiovascular/pulmonary disease and GI disorders. Indeed, despite the knowledge of potential immunomodulatory properties of these compounds, no AChE inhibitor is currently indicated for the treatment of conditions other than neurological/neurodegenerative disorders.

Ladostigil

Ladostigil, also referred to as R(+)-6-(N-methyl, N-ethyl-carbamoyloxy)-N'-propargyl-1-aminoindan and (3R)-3-(prop-2-ynylamino)-2,3,-dihydro-1H-indan-5-ylethyl methyl carbamate, is a propargyl-aminoindan with a carbamate moiety. Designed to combine the MAO-B inhibitory activity of rasagiline with AChE inhibitory activity of rivastigmine, ladostigil inhibits AChE and both MAO-A and B selectively in the brain. At much lower doses than those that inhibit either enzyme in vivo ladostigil has neuroprotective activity associated with a reduction of oxidative stress and microglial activation, neither of which is related to the ability to inhibit MAO or AChE.

Salts of ladostigil include the ½ L-tartrate salt of ladostigil. This tartrate salt of ladostigil, ladostigil tartrate-6-(N-ethyl, N-methyl carbamyloxy)-N-propargyl-1(R)-aminoindan, tartaric acid (2:1) abbreviated as [(R)-CPAI] tartrate and also referred to as ladostigil tartrate, has CAS registry number 209394-46-7 and may be used as the active ingredient of ladostigil tablets.

Ladostigil's activities include the inhibition of AChE and the inhibition of MAO. In vivo, ladostigil inhibits both MAO-A and MAO-B selectively in the brain. These activities make ladostigil particularly useful in the treatment of Alzheimer's disease comorbid with dementia.

U.S. Pat. Nos. 6,251,938, 6,303,650, and 6,538,025, incorporated herein by reference, disclose ladostigil and other compounds that inhibit AChE and MAO selectively in the brain. These compounds may be useful to treat Alzheimer's disease and other dementias such as senile dementia, dementia of the Parkinson's type, vascular dementia and Lewy body dementia, in addition to depression.

U.S. Pat. No. 7,335,685 and U.S. Application Publication Nos. 20060189819, 20070088082 and 20070093549, incorporated herein by reference, disclose crystalline forms of ladostigil tartrate and methods of producing the same. U.S. Pat. Nos. 7,375,249 and 7,476,757, and U.S. Application Publication No. 20060199974, incorporated herein by reference, disclose synthesis of enantiomeric indanylamine derivatives including ladostigil. U.S. Pat. No. 7,491,847 and U.S. Application Publication No. 20070112217, incorporated herein by reference, disclose methods for isolating propargylated aminoindans. U.S. Application Publication No. 20070203232, incorporated herein by reference, discloses methods for isolating propargylated aminoindans and discloses their use in the treatment of Alzheimer's disease. U.S. Application Publication No. 20070232691, incorporated herein by reference, discloses the use of ladostigil to treat schizophrenia.

U.S. Application Publication No. 20060189685, incorporated herein by reference, discloses formulations comprising ladostigil. U.S. Application Publication Nos. 20070135518 and 20070293583, incorporated herein by reference, discloses the use of low doses of ladostigil for neuroprotection.

WO 2005/051371 discloses a method for treatment of a subject susceptible to or suffering from a cardiovascular disorder or disease which comprises administering to the subject an amount of an active agent selected from the group consisting of propargylamine, a propargylamine derivative, and a pharmaceutically acceptable salt thereof, effective to treat the subject. Ladostigil is identified as an N-propargyl-1-aminoindan analog.

WO 2006/130726 discloses methods for the treatment of a form of multiple sclerosis comprising administering an amount of R(+)-6-(N-methyl, N-ethyl-carbamoyloxy)-N'-propargyl-1-aminoindan or a pharmaceutically acceptable salt thereof. WO '726 further discloses that ladostigil doses that were effective in ameliorating EAE (51 and 70.1 mg/kg/day) exerted 47-52% inhibition of AChE in brain and 60-65% inhibition of AChE in blood, while lower doses were not found to be effective.

WO 2012/059920, published after the priority date of the present application, relates to methods of treating individuals who have been identified as having Alzheimer's disease and other neurodegenerative diseases comprising administration of ladostigil or a pharmaceutically active salt thereof in a dosage in the range of 60-200 mg ladostigil per day.

Panarsky et al. (2010) discloses that in vitro treatment by ladostigil and three of its active metabolites decreased the release of NO from microglial cell cultures induced by LPS. The disclosure suggests that the both the carbamate moiety and propargyl moiety might not be necessary for their protective activity against LPS in microglia. The amounts of mRNA of IL-1β and TNFα in response to LPS were also reduced following ladostigil treatment.

Panarsky et al. (2012), published after the priority date of the present application, disclose that ladostigil (1 mg/kg/day) significantly decreased the gene expression of IL-1β, IL-6, TNF-α and inducible NO synthase (iNOS) in the parietal cortex. It was also shown that in vitro treatment by ladostigil and three of its active metabolites inhibited the release of NO induced by LPS from mouse microglial cells and reduced TNF-α mRNA and protein and IL-1β and iNOS mRNA.

However, none of the art discloses or fairly suggests that ladostigil may be useful as a therapeutic drug for non-neurological indications, such as for treating inflammatory diseases in peripheral organs outside the central nervous system. There remains a need for methods and formulations of ladostigil and pharmaceutically acceptable salts thereof which can effectively inhibit inflammation without the devastating side effects associated with marketed anti-inflammatory drugs. In particular, there remains an unmet medical need for therapies for pathologies associated with systemic inflammation, including e.g. gastrointestinal inflammation and inflammation associated with type 2 diabetes. Means for protecting against ischemic damage induced e.g. by surgical intervention is an unmet need.

SUMMARY OF THE INVENTION

The invention relates to pharmaceutical compositions and dosage units comprising ladostigil and to methods of using same for inhibiting inflammation. Specific embodiments of the invention relate to the use of ladostigil for treating inflammation by counteracting the activity of key inflammatory mediators or inhibiting the release of inflammatory mediators from inflammatory inducing cells. The invention further provides novel therapeutic modalities for ameliorating systemic inflammation, including septic shock and inflammatory conditions affecting the gastrointestinal, myocardial and endocrine systems, as well as other IL-6 mediated pathologies.

The present invention is based, in part, on the surprising discovery that ladostigil exerts beneficial therapeutic effects outside the central nervous system (CNS). It is now demonstrated for the first time, that ladostigil possesses anti-inflammatory effects that are unrelated to its MAO and AChE inhibition activities, or to its reported activity on microglial cells. Ladostigil is demonstrated herein to be effective in several in vivo models, including experimental endotoxemia, ulcerative colitis and diabetes mellitus, and in reducing the levels of pro-inflammatory mediators, notably IL-6. Ladostigil was surprisingly found to be superior to other agents such as rivastigmine, providing both increased efficacy and enhanced safety in various in vivo models of systemic inflammation.

The present invention is further based, in part, on the finding that these anti-inflammatory activities were significant at doses that cause minimal or no MAO or AChE inhibition, while higher doses were surprisingly found to be inferior, or even ineffective in certain experimental models. This unexpected anti-inflammatory pharmacokinetic profile of ladostigil indicates the advantage of administrating doses of ladostigil in the range of 10-60 mg per day while at least minimizing or even abolishing side effects associated with the inhibition of MAO and/or AChE activity.

It was further discovered surprisingly that ladostigil is able to enhance the efficacy of myocardial ischemic preconditioning (IPC) protocols in rats, demonstrating for the first time enhanced protection against ischemia/reperfusion injury in aged subjects, not previously amenable for treatment.

Thus, provided in various embodiments of the invention are methods for inhibiting inflammation, specifically systemic inflammation, in a subject in need thereof. In other embodiments disclosed are methods for the treatment, prevention or amelioration of inflammatory diseases, as detailed below. The methods of the invention are affected by administering to a subject in need thereof ladostigil or a pharmaceutically active salt thereof.

According to one aspect, there is provided a method for inhibiting inflammation in a subject in need thereof, comprising administering to the subject ladostigil or a pharmaceutically active salt thereof, thereby inhibiting inflammation in said subject.

In one embodiment, the inflammation is systemic inflammation (not localized to the CNS). In another embodiment, the subject is identified as being afflicted with an inflammatory disease other than a neurological inflammatory disease. In another embodiment, the subject is not concomitantly afflicted with a neurological or neurodegenerative disease. In another embodiment, the inflammatory disease is mediated by elevated IL-6 levels (e.g. characterized by enhanced IL-6 blood levels).

In various embodiments, the inflammatory disease is selected from the group consisting of an inflammatory gastrointestinal disease (e.g. colitis), an inflammatory metabolic disease (e.g. diabetes), and ischemia-associated inflammation (e.g. myocardial post-ischemic inflammation).

In certain particular embodiments, the inflammatory gastrointestinal disease includes, but is not limited to, inflammatory bowel diseases (e.g. ulcerative colitis and Crohn's disease) irritable bowel syndrome, ileitis, chronic inflammatory intestinal disease, and celiac disease.

In other particular embodiments, the inflammatory metabolic disease is type 1 diabetes, type 2 diabetes, pre-diabetes, dyslipidemia, or insulin resistance. In another particular embodiment the disease is type 2 diabetes.

In another embodiment, said subject in need thereof is a subject afflicted with, or at risk for developing, endotoxemia or septic shock. In a particular embodiment, the subject is afflicted with septic shock.

Advantageously, the methods of the invention inhibit inflammation in a subject while inducing minimal side effects associated with the inhibition of cholinesterase activity (if any). In another embodiment, said inhibiting inflammation further comprises minimizing side effects associated with the inhibition of cholinesterase activity. In another embodiment, said ladostigil is administered in an amount that inhibits no more than 25% acetylcholinesterase activity, monoamine oxidase activity, or the combined activities of both enzymes. In another embodiment, said ladostigil is administered in an amount that inhibits no more than 15% acetylcholinesterase activity, monoamine oxidase activity, or the combined activities of both enzymes. In another embodiment said ladostigil is administered at a daily dose of 10 to 60 mg. In another embodiment, said pharmaceutically active salt thereof is ladostigil tartrate.

In another embodiment, said inhibiting inflammation reduces: the blood level of TNF-α, the blood level of IL-β1, the blood level of IL-6, the spleen level of TNF-α, the spleen level of IL-β1, the spleen level of IL-6 or any combination thereof. In a particular embodiment, said inhibiting inflammation comprises reducing the blood level of IL-6. In another embodiment, said inhibiting inflammation comprises inhibiting the release of IL-6.

According to various embodiments of the invention, ladostigil may be administered to said subject e.g. in one daily dose of ladostigil, or in other embodiments to two daily doses of ladostigil. For example, the two daily doses may be equally divided doses. In another embodiment, said ladostigil or said pharmaceutically active salt thereof is formulated in an oral dosage form. In another embodiment, said ladostigil or said pharmaceutically active salt thereof is formulated in a rectal dosage form, e.g. for the treatment of gastrointestinal inflammatory diseases. In another embodiment, said ladostigil or a pharmaceutically active salt thereof is formulated in an immediate release pharmaceutical composition. In another embodiment the methods of the invention comprise administering said ladostigil as a sole active ingredient. In yet another embodiment, the methods comprise administering said ladostigil in combination, with another treatment or active ingredient, e.g. an ischemic conditioning therapy, as detailed below.

In another aspect, the invention provides a method of treating an inflammatory disease of the gastrointestinal tract in a subject in need thereof, comprising administering to the subject ladostigil or a pharmaceutically active salt thereof, thereby treating the disease. In another embodiment, the disease is a chronic inflammatory disease associated with pathological inflammation of the gastrointestinal tract. In certain particular embodiments, the inflammatory gastrointestinal disease includes, but is not limited to, inflammatory bowel diseases (e.g. ulcerative colitis and Crohn's disease) irritable bowel syndrome, ileitis, chronic inflammatory intestinal disease, and celiac disease. In certain embodiments, said ladostigil is administered at a daily dose of 10 to 60 mg. In certain other embodiments, said ladostigil is administered in an amount that inhibits no more than 25% or in other embodiments no more than 15% acetylcholinesterase activity, monoamine oxidase activity, or the combined activities of both enzymes.

In another aspect, there is provided a method of treating an inflammatory metabolic disease in a subject in need thereof, comprising administering to the subject ladostigil or a pharmaceutically active salt thereof, thereby treating the disease. In various embodiments, the disease includes, but is not limited to, diabetes mellitus (e.g. type 1 or type 2), pre-diabetes, dyslipidemia, and insulin resistance. In a particular embodiment, the disease is type 2 diabetes mellitus.

In another aspect, the invention provides a method of reducing or inhibiting ischemic injury (in particular, ischemic myocardial injury) in a subject in need thereof comprising administering to the subject ladostigil, thereby reducing or inhibiting ischemic injury in said subject. Preferably, ladostigil is administered to said subject in combination with ischemic conditioning (e.g. prior to, concurrently with or after a conditioning treatment). For example, ladostigil may be chronically administered at a daily dose of 10-60 mg to said subject for two weeks prior to conditioning and may be continued after preconditioning, e.g. myocardial IPC performed by mechanical arterial occlusion to induce repeated cycles of brief ischemic episodes. Advantageously, the subject is an aged or diabetic subject, not otherwise amenable for ischemic conditioning.

In various embodiments, the method may be used for reducing or inhibiting an ischemia-associated inflammation (e.g. myocardial post-ischemic inflammation), for reducing or inhibiting perioperative myocardial ischemic damage, for protecting against ischemic and/or reperfusion injury, for providing cardioprotection prior to, during, or following cardiac surgery or ischemic attack, and for enhancing the efficacy of ischemic conditioning in a subject in need thereof. In certain embodiments, said ladostigil is administered at a daily dose of 10 to 60 mg. In certain other embodiments, said ladostigil is administered in an amount that inhibits no more than 25% or in other embodiments no more than 15% acetylcholinesterase activity, monoamine oxidase activity, or the combined activities of both enzymes.

In another aspect, there is provided a pharmaceutical composition comprising ladostigil or a pharmaceutically active salt thereof, in combination with an ischemic conditioning therapy, selected from the group consisting of erythropoietin, an opioid (e.g. morphine, sufentanil, remifentanil, methadone), insulin and an adenosine A1, A2A, A2B and/or A3 receptor agonist (e.g. adenosine, 5'-N-ethylcarboxamidoadenosine, N6-Cyclopentyladenosine, 2-(1-Hexynyl)-N-methyladenosine). In a particular embodiment, the composition comprises 10 to 60 mg ladostigil in unit dosage form.

In another aspect there is provided a pharmaceutical pack, comprising ladostigil or a pharmaceutically active salt thereof, and an ischemic conditioning therapy, selected from the group consisting of erythropoietin, an opioid, insulin and an adenosine 2 receptor, with instructions for administering ladostigil and the ischemic conditioning therapy in concurrent or sequential combination for reducing or inhibiting ischemic injury. In a particular embodiment, the pharmaceutical pack comprises 10 to 60 mg ladostigil in unit dosage form.

In another aspect the invention provides a pharmaceutical composition for use in inhibiting systemic inflammation in a subject in need thereof, comprising ladostigil or a pharmaceutically active salt thereof. In another embodiment the composition is for use in inhibiting inflammation in a subject afflicted with an inflammatory disease selected from the group consisting of an inflammatory gastrointestinal disease, an inflammatory metabolic disease and ischemia-associated inflammation. In another embodiment the disease is an inflammatory gastrointestinal disease selected from the group consisting of inflammatory bowel diseases (ulcerative colitis and Crohn's disease), irritable bowel syndrome, ileitis, chronic inflammatory intestinal disease, and celiac disease. In another embodiment the disease is an inflammatory metabolic disease selected from the group consisting of type 2 diabetes, type 1 diabetes, pre-diabetes, dyslipidemia and insulin resistance. In another embodiment said disease is septic shock. In another embodiment the inflammatory disease is mediated by elevated IL-6 levels. In another embodiment said ladostigil is at a daily dose of 10 to 60 mg. In another embodiment said ladostigil is an amount that inhibits no more than 25% acetylcholinesterase activity, monoamine oxidase activity, or the combined activities of both enzymes, or in an amount that inhibits no more than 15% acetylcholinesterase activity, monoamine oxidase activity, or the combined activities of both enzymes. In another embodiment said pharmaceutically active salt thereof is ladostigil tartrate.

In another aspect there is provided a pharmaceutical composition comprising ladostigil or a pharmaceutically active salt thereof for use in treating an inflammatory disease in a subject in need thereof, wherein said disease is an inflammatory disease of the gastrointestinal tract or an inflammatory metabolic disease. In another embodiment the disease is a chronic inflammatory disease associated with pathological inflammation of the gastrointestinal tract, preferably selected from the group consisting of inflammatory bowel diseases (ulcerative colitis and Crohn's disease) irritable bowel syndrome, ileitis, chronic inflammatory intestinal disease, and celiac disease. In another embodiment the disease is an inflammatory metabolic disease selected from the group consisting of type 2 diabetes mellitus, type 1 diabetes mellitus, pre-diabetes, dyslipidemia, and insulin resistance, preferably type 2 diabetes mellitus.

In another aspect there is provided a pharmaceutical composition for use in reducing or inhibiting ischemic injury, preferably ischemic myocardial injury, in a subject in need thereof, comprising ladostigil or a pharmaceutically active salt thereof. In another embodiment the composition is used in combination with ischemic conditioning. In another embodiment the composition is used for reducing or inhibiting perioperative myocardial ischemic damage, or for enhancing the efficacy of ischemic conditioning in a subject in need thereof. In another embodiment the subject is an aged or diabetic subject, not otherwise amenable for ischemic conditioning. In another embodiment the composition comprises ladostigil or a pharmaceutically active salt thereof in combination with an ischemic conditioning therapy, selected from the group consisting of erythropoietin, an opioid, insulin and an adenosine A1, A2A, A2B and/or A3 receptor agonist.

In another embodiment said ladostigil is administered at a daily dose of 10 to 60 mg. In another embodiment said ladostigil is in an amount that inhibits no more than 15% acetylcholinesterase activity, monoamine oxidase activity, or the combined activities of both enzymes.

Other objects, features and advantages of the present invention will become clear from the following description and drawings.

DETAILED DESCRIPTION OF THE INVENTION

Figure 1:
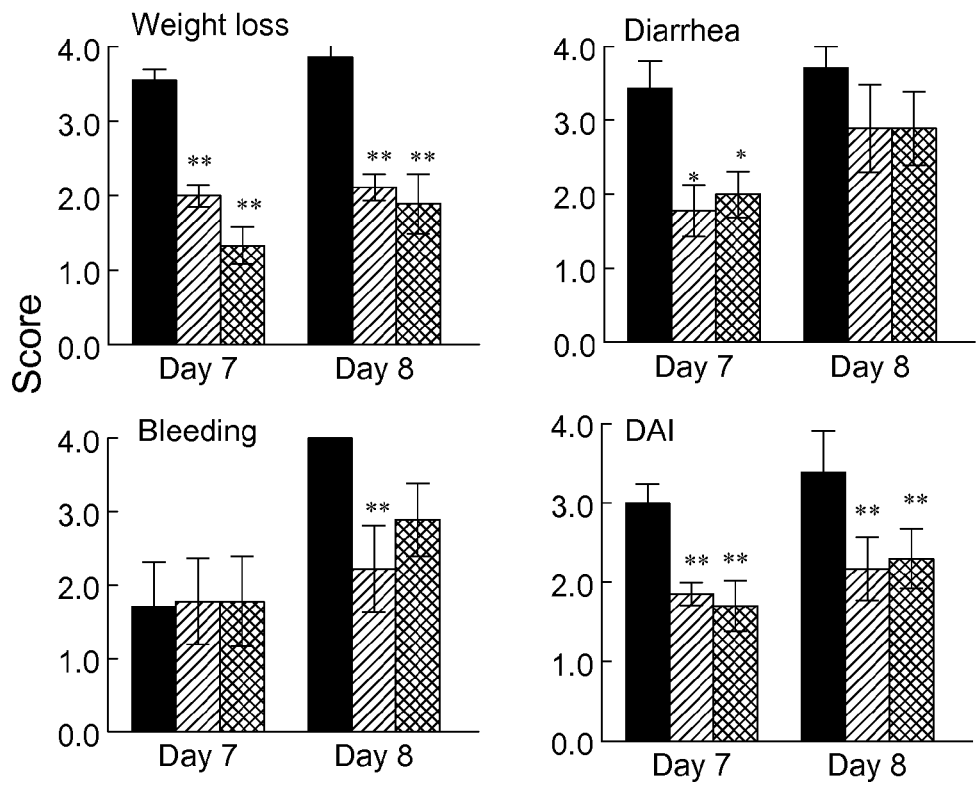
FIG. 1 shows the effect of ladostigil on macroscopic parameters of colitis on days 7 and 8 of treatment with 5% DSS.

The present invention relates to pharmaceutical compositions and dosage units comprising ladostigil or active salts thereof and methods of using the same for inhibiting inflammation via inhibiting the release of inflammatory mediators. In another embodiment, inhibiting inflammation is neutralization the reactivity of inflammatory mediators.

The present invention further provides pharmaceutical compositions comprising ladostigil or its pharmaceutically acceptable salts useful for inhibition of systemic inflammation. This compound was known for the treatment of Alzheimer's disease and other forms of dementia. The present invention provides novel uses of compositions comprising ladostigil for treating and inhibiting the progression of inflammatory diseases, particularly inflammatory conditions affecting the gastrointestinal, myocardial and endocrine systems, as well as other IL-6 mediated pathologies. In other words, the present invention is directed to treatment of a subject not otherwise in need of treatment with ladostigil. The methods of the invention are advantageously affected by administering ladostigil or salts thereof at doses that cause minimal or no MAO or AChE inhibition, thereby minimizing adverse effects associated with inhibition of these enzymes.

As detailed below, the anti-inflammatory properties of ladostigil were examined in the peripheral system of mice and other mammals. In certain experiments, endotoxemia was induced by injection of LPS. A single oral administration of ladostigil (10 mg/kg) was much more effective than one of 20 mg/kg in decreasing the formation of pro-inflammatory cytokines TNF-α, IL-1β and IL-6 in the spleen. This was accomplished without any significant inhibition of ChE in the brain, plasma or spleen. In other experiments, chronic oral administration of ladostigil (5 or 10 mg/kg/day) reduced the symptoms of UC and inflammatory markers in the colon induced by dextran sodium sulphate (DSS) without causing any inhibition of colonic ChE. These findings are in direct contrast to observations with a ChE inhibitor, rivastigmine that only showed anti-inflammatory activity in the LPS endotoxemia and mouse DSS models at a dose that inhibited ChE in the spleen, colon and brain by >50%. In addition, ladostigil was shown to exert unexpectedly improved anti-inflammatory activity compared to rivastigmine in preventing weight loss associated with gastrointestinal inflammation. Thus, ladostigil provide both enhanced efficacy and improved safety compared to ChE inhibitors.

In one embodiment, the invention provides a method for inhibiting inflammation, specifically systemic inflammation, in a subject, comprising administering to the subject, a therapeutically effective amount of ladostigil or a pharmaceutically active salt thereof, thereby inhibiting inflammation in a subject in need thereof.

In other embodiments, provided herein are methods for treating an inflammatory disease of the gastrointestinal tract or an inflammatory metabolic disease in a subject in need thereof, methods of reducing or inhibiting ischemic injury in a subject in need thereof, and compositions and pharmaceutical packs comprising ladostigil or a pharmaceutically active salt thereof in combination with an ischemic conditioning therapy, selected from the group consisting of erythropoietin, an opioid, insulin and an adenosine A1, A2A, A2B and/or A3 receptor agonist, as detailed below.

The compositions and methods of the invention advantageously comprise the use of ladostigil at therapeutically effective amounts that inhibit inflammation while reducing side effects associated with the inhibition of AChE and/or MAO activities, as detailed below.

According to some embodiments, the methods of the invention comprise identifying the subject as being afflicted with, or in other embodiments, at risk for developing, the inflammatory disease, and administering to said subject a therapeutically effective amount of ladostigil or a pharmaceutically active salt thereof, thereby treating or inhibiting the progress of said disease.

Inhibition of Inflammation and Inflammatory Mediators

Inflammatory diseases are associated with reactions of both the specific and non-specific defense systems. A specific defense system reaction is a specific immune system reaction response to an antigen (possibly including an autoantigen), e.g. reactions mediated by B cells and T cells. A non-specific defense system reaction is an inflammatory response mediated by leukocytes incapable of immunological memory. Such cells include granulocytes, macrophages, neutrophils and eosinophils. Inflammation is associated with activation of a large array of enzymes, increase in vascular permeability and extravasation of blood fluids, cell migration and release of chemical mediators. Various inflammatory mediators involved in such inflammatory reactions or inflammatory cascades are known, including, but not limited to, cytokines, chemokines and acute phase proteins. Assays for inflammation are well known in the art. Without wishing to be bound by any theory or mechanism of action, the immunomodulatory effect of the compounds of the invention may be determined by one or more such inflammatory parameters, including, but not limited to, leukocyte and lymphocyte (e.g. T cell) activation, proliferation, migration and infiltration into inflammatory sites. Conveniently, the efficacy of ladostigil and its salts in inhibiting inflammation may be determined using in vitro and/or in vivo assays, as exemplified below. For example, the ability of the compound to reduce increased IL-6 levels (e.g. blood levels) associated with an inflammatory disease may be used to determine an anti-inflammatory effect of the compound in ameliorating the disease.

In one embodiment, there is provided method for inhibiting inflammation in a subject in need thereof, comprising administering to said subject, ladostigil or a pharmaceutically active salt thereof, thereby inhibiting inflammation in a subject in need thereof. In another embodiment, inhibiting inflammation is treating a subject afflicted with inflammation. In another embodiment, inhibiting inflammation is inhibiting the progression/deterioration of the inflammatory process. In another embodiment, inhibiting inflammation is reducing the risk of septic shock. In another embodiment, inhibiting inflammation is inhibiting elevation in the level of pro-inflammatory cytokines (such as: TNF-alpha, IL-6, IL-1 beta) in the blood and/or spleen. In another embodiment, inhibiting inflammation is inhibiting elevation in the level of pro-inflammatory cytokines (such as: TNF-alpha, IL-6, IL-1 beta) in the blood and/or spleen during inflammation. In another embodiment, inhibiting inflammation is inhibiting the elevation in the level of pro-inflammatory cytokines (such as: TNF-alpha, IL-6, IL-1 beta) in the blood and/or spleen by at least 20%. In another embodiment, inhibiting inflammation is inhibiting a trigger for systemic inflammation. In another embodiment, inhibiting inflammation is inhibiting the spread of a local inflammation into systemic inflammation. In another embodiment, inhibiting inflammation is inhibiting the progression of systemic inflammation. Each possibility represents a separate embodiment of the invention.

In another embodiment, inflammation is systemic inflammation. In another embodiment, systemic inflammation is the result of release of pro-inflammatory cytokines from immune-related cells and the chronic activation of the innate immune system. In another embodiment, systemic inflammation is chronic systemic inflammation.

In another embodiment, inflammation is systemic inflammatory response syndrome (SIRS). In another embodiment, systemic inflammatory response syndrome is an inflammatory state affecting the whole body, frequently a response of the immune system to infection, but not necessarily so. In another embodiment, systemic inflammatory response syndrome is related to sepsis, a condition in which individuals both meet criteria for SIRS and have a known or highly suspected infection. In another embodiment, inflammation is an acute inflammatory response. In another embodiment, systemic inflammation is an acute inflammatory response.

In another embodiment, inflammation is systemic inflammatory response syndrome. In another embodiment, inflammation according to the invention is septic shock. In another embodiment, inflammation according to the invention leads to septic shock. In another embodiment, the invention provides a method for inhibiting or preventing systemic inflammation in a subject, comprising administering to the subject, a therapeutically effective amount of ladostigil or a pharmaceutically active salt thereof. In another embodiment, the invention provides a method for inhibiting or preventing septic shock in a subject, comprising administering to the subject, a therapeutically effective amount of ladostigil or a pharmaceutically active salt thereof. In another embodiment, a systemic inflammation response syndrome is a septic shock or results in a septic shock. In another embodiment, the subject is afflicted with endotoxemia. As used herein, the term "endotoxemia" refers to a condition in which endotoxins (LPS particles or molecules) are present in a subject at levels capable of inducing specific responses, such as sepsis and septic shock. Generally, endotoxemia is associated with a gram-negative bacterial infection.

In another embodiment, inflammation is a chronic inflammatory disease. In another embodiment, inflammation is polyarteritis nodosa. In another embodiment, inflammation is a disease related to a bacterial, a fungal or a viral infection or may be an eclampsia.

In another embodiment, inflammation according to the invention is septic shock associated with bacteremia, funguemia, parasitemia, viremia, associated with multiple organ failure. In another embodiment, inflammation according to the invention is severe sepsis, (such as but not limited to: peritonitis, pneumonia, catheter related infection, urinary, biliary tract infection or malaria). In another embodiment, inflammation according to the invention is caused by: pancreatitis, burns, polytrauma associated or not with fat embolism, massive transfusion, adult respiratory distress syndrome (ARDS), acute renal failure (ARF) related to inflammatory disease, or surgery. In another embodiment, inflammation according to the invention can result in multiple organ dysfunction and severe hypo-perfusion: i.e. hemorrhagic, cardiogenic, anaphylactic ischemia-reperfusion: crush syndrome, aortic cross clamping, ischemia with reperfusion (i.e. mesenteric, lower limb ischemia). Each possibility represents a separate embodiment of the invention.

In another embodiment, inflammation according to the invention is chronic infection such as but not limited to: HIV, endocarditis and an infection related arteritis i.e. syphilis. In another embodiment, inflammation is a systemic disease such as: necrotizing angiitis, Wegner's syndrome, polyarteritis nodosa, allergic granulomatosis, temporal arteritis, nephroangiosclerosis, Takayasus's disease, Buerger's disease, autoimmune diseases: e.g. rheumatoid arthritis, systemic lupus erythematosus (SLE), acute rheumatic fever, dennatomyositis, systemic scleroderma, thrombotic thrombocytopenic purpura, hematologic and cancerologic diseases-associated with elevated cytokines (i.e. TNF-alpha) or tumoral lysis, or endothelium aggression Kahler's disease, Lymphoma especially T cell Lymphoma, tumoral lysis syndrome either spontaneous or induced by anti-carcinogenic treatment in hematologic or tumoral diseases (i.e. acute leukemia, solid tumor especially with elevated cytokines). In another embodiment, inflammation according to the invention results from immune diseases (i.e. Berger's disease) atherosclerosis, post-operative vascular restenosis following vascular angioplasty, diabetes (e.g. diabetic angiitis), severe liver diseases, or inflammatory bowel disease (IBD). In a particular embodiment, said disease is an autoimmune disease. Each possibility represents a separate embodiment of the invention.

In another embodiment, the present invention utilizes a well-known model wherein systemic inflammation is induced by lipopolysaccharide (LPS). In another embodiment, LPS is used for inducing septic shock.

In another embodiment, the invention relates to inhibition of systemically increased levels of inflammatory mediators such as cytokines. This embodiment is unrelated to previous reports on the effect of ladostigil on release of cytokines from microglial cells, inter alia since the latter does not typically result in elevated levels of cytokines outside the brain, such as in the blood. In another embodiment, the invention provides a method for reducing: the blood level of TNF-α, the blood level of IL-β1, the blood level of IL-6, the spleen level of TNF-α, the spleen level of IL-β1, the spleen level of IL-6, or any combination thereof, in a subject in need thereof, comprising administering to the subject, a therapeutically effective amount of ladostigil or a pharmaceutically active salt thereof. In another embodiment, a subject in need thereof is a subject afflicted with inflammation. In another embodiment, a subject in need thereof is a subject afflicted with systemic inflammation. In another embodiment, a subject in need thereof is a subject afflicted with septic shock. In another embodiment, a subject in need thereof is a subject afflicted with a disease associated with inflammation and/or systemic inflammation. In another embodiment, a subject in need thereof is a subject having an elevated blood and/or spleen level of TNF-α, IL-β1, IL-6, or any combination thereof. In another embodiment, a subject in need thereof is a subject having an elevated blood and/or spleen level of TNF-α, IL-β1, IL-6, or any combination thereof due to inflammation. Each possibility represents a separate embodiment of the invention.

In another embodiment, systemic inflammation and/or septic shock are associated with elevated blood and/or spleen levels of IL-β1, IL-6, and TNF-α. In another embodiment, reducing the systemic levels of IL-β1, IL-6, and TNF-α ameliorates the systemic inflammatory disease of the invention. In another embodiment, reducing the systemic levels of IL-β1, IL-6, and TNF-α reduces the risk of secondary complication that may result in death. In another embodiment, reducing the systemic levels of IL-β1, IL-6, and TNF-α reduces the risk of septic shock.

Another aspect of the present invention relates to methods for inhibiting inflammation in a subject in need thereof, comprising administering to the subject, a daily dose of 10 to 60 mg ladostigil or a pharmaceutically active salt thereof.

Another aspect of the present invention relates to methods for inhibiting inflammation in a subject in need thereof, comprising administering to the subject, a daily dose of 10 to 100 mg ladostigil or a pharmaceutically active salt thereof, wherein the daily dose induces minimal side effects associated with the inhibition of cholinesterase activity.

Another aspect of the present invention relates to methods for inhibiting inflammation in a subject in need thereof, comprising administering to the subject, a daily dose of 10 to 60 mg ladostigil or a pharmaceutically active salt thereof, wherein the daily dose is refractory in inhibiting MAO and/or cholinesterase (ChE) activities.

Another aspect of the present invention relates to methods for inhibiting inflammation in a subject in need thereof, comprising administering to the subject, a daily dose of 10 to 100 mg ladostigil or a pharmaceutically active salt thereof, wherein the daily dose has minimal MAO and/or ChE inhibiting activities.

Another aspect of the present invention relates to methods for inhibiting inflammation with ladostigil by inhibiting the release of: NO, IL-6, TNF-α, IL-β1, iNOS, or any combination thereof from cells that induce inflammation.

In another embodiment, the inflammation is systemic inflammation.

It is to be understood, that ladostigil is known as being useful for treating a subject suffering from Alzheimer's disease, dementia, mild cognitive impairment, Parkinson's disease, age-related macular degeneration, and amyotrophic lateral sclerosis (US 2007/0135518). Ladostigil has also been suggested to be useful in the treatment of multiple sclerosis (MS) (WO 2006/130726), schizophrenia (US 2007/0232691), Huntington's disease, ataxia telangiectasia, Batten disease, corticobasal degeneration, Amnesia, aphasia, Creutzfeldt-Jakob disease, Fatal familial insomnia, infantile refsum disease, Lyme disease, Machado-Joseph disease, Multiple system atrophy, Niemann-Pick disease, associated with Protein aggregation, Refsum disease, Sandhoff disease, Shy-Drager syndrome, Spinocerebellar ataxia, Subacute combined degeneration of spinal cord, Tabes dorsalis, Tay-Sachs disease, Toxic encephalopathy, and Wobbly hedgehog syndrome (WO 2012/059920). The treatment of any of these diseases is excluded from the scope of the present invention. In other embodiments, the use of ladostigil for preventing the development of these diseases is excluded from the scope of the present invention. Preferably, the subject treated by the methods of the present invention does not suffer simultaneously from any of the aforementioned diseases.

In another embodiment, the present invention is based, inter-alia, on the surprising finding that ladostigil has a systemic anti-inflammatory effect which extends beyond its known CNS anti-inflammatory effect. In another embodiment, the systemic anti-inflammatory effect is materially different from a local CNS anti-inflammatory effect. In another embodiment, the systemic anti-inflammatory effect includes the inhibition of key blood/spleen inflammatory cytokines such as IL-6. Therefore, the term "systemic inflammation" as used herein refers to an inflammatory response involving major organs or symptoms outside the CNS. According to further embodiments, "systemic inflammation" excludes CNS inflammation, induced or mediated by microglial cells and other resident cells within the brain. Yet, according to certain other embodiments, the invention provides improved methods for inhibiting inflammation that is partially manifested in nervous tissue, affected by administering preferred ladostigil doses as described herein.

In another embodiment, the invention relates to a method for inhibiting systemic inflammation in a subject in need thereof, comprising administering to the subject ladostigil or a pharmaceutically active salt thereof, thereby inhibiting inflammation. In another embodiment, the subject is afflicted with an inflammatory disease. In another embodiment, the inflammatory disease is mediated by enhanced IL-6 levels (e.g. characterized by enhanced IL-6 blood levels). In various particular embodiments, the inflammatory disease is an inflammatory gastrointestinal disease (e.g. colitis), an inflammatory metabolic disease (e.g. diabetes), or ischemia-associated inflammation (e.g. myocardial post-ischemic inflammation), as detailed further below.

In another aspect, the invention provides a method of treating an inflammatory disease (e.g. a systemic inflammatory disease) in a subject in need thereof, comprising administering to the subject ladostigil or a pharmaceutically active salt thereof, thereby treating the disease. In various particular embodiments, the inflammatory disease is an inflammatory gastrointestinal disease (e.g. colitis), an inflammatory metabolic disease (e.g. diabetes), or ischemia-associated inflammation (e.g. myocardial post-ischemic inflammation), as detailed further below.

The term "treating" refers to administering a therapy in amount, manner, and/or mode effective to improve a condition, symptom, or parameter associated with a disease or to prevent progression of a disease, to either a statistically significant degree or to a degree detectable to one skilled in the art. The terms "treating" and "treatment" also include reduction in severity and/or frequency of symptoms, elimination of symptoms and/or underlying cause, prevention of the occurrence of symptoms and/or their underlying cause, and improvement or remediation of damage. With respect to inflammatory diseases, the term further includes slowing or preventing progression of deterioration due to inflammatory processes. An effective amount, manner, or mode can vary depending on the subject and may be tailored to the subject.

Diabetes and Inflammatory Metabolic Diseases

According to some embodiments, the methods of the invention relate to the use of ladostigil for the treatment of a subject identified as afflicted with diabetes. As used herein, the term "Type 2 diabetes", also and interchangeably referred to as "non-insulin dependent diabetes mellitus (NIDDM)", or T2D refers to the disorder characterized by cellular resistance to insulin and/or secretion of less insulin than is necessary to keep blood glucose levels in balance. "Type 1 diabetes", in contrast, refers to a disorder characterized by the destruction of insulin producing beta cells in the pancreas by an autoimmune reaction.

In other embodiments, the invention relates to inhibiting the progression or deterioration of diabetes. In other embodiments, the treatment of subjects at risk of developing T2D, such as those afflicted with pre-diabetes, insulin resistance or other inflammatory metabolic diseases or conditions that precede the onset of T2D, is further contemplated. T2D is often characterized by hyperglycemia manifested by a fasting blood sugar of higher than 140 mg/dL. The term "pre-diabetes" as used herein refers to a condition characterized by a fasting blood sugar of higher than 100 mg/dL, but below 140 mg/dL. The term "insulin resistance" as used herein refers to a condition characterized by a reduced sensitivity to insulin in the whole body or individual tissues, including skeletal muscle, myocardium, adipose tissue, and liver. The term "dyslipidemia" as used herein refers to a condition in which at least one of triglycerides, free fatty acids, total cholesterol, and LDL-cholesterol is at a level considered above normal. In another embodiment, the methods relate to the use of ladostigil for inhibiting a diabetic sign or symptom, e.g. for preventing or inhibiting hyperglycemia. According to another aspect, there is provided a method for inhibiting inflammation in a subject in need thereof, comprising administering to the subject ladostigil or a pharmaceutically active salt thereof, thereby inhibiting inflammation in said subject, wherein the subject is afflicted with an inflammatory metabolic disease. In another embodiment, the subject is identified as being afflicted with an inflammatory metabolic disease. In another embodiment, the method comprises identifying the subject as being afflicted with an inflammatory metabolic disease, and administering ladostigil or a pharmaceutically active salt thereof to said subject identified as being afflicted with an inflammatory metabolic disease.

According to particular embodiments, the inflammatory metabolic disease includes, but is not limited to, type 2 diabetes, type 1 diabetes, pre-diabetes, dyslipidemia, or insulin resistance.

In another aspect, there is provided a method of treating an inflammatory metabolic disease in a subject in need thereof, comprising administering to the subject ladostigil or a pharmaceutically active salt thereof, thereby treating the disease. In various embodiments, the disease includes, but is not limited to, type 2 diabetes mellitus, type 1 diabetes mellitus, pre-diabetes, dyslipidemia, and insulin resistance. In a particular embodiment, the disease is type 2 diabetes mellitus. In another particular embodiment, the disease is type 1 diabetes mellitus. In another embodiment, the subject is identified as being afflicted with an inflammatory metabolic disease. In another embodiment, the method comprises identifying the subject as being afflicted with an inflammatory metabolic disease, and administering ladostigil or a pharmaceutically active salt thereof to said subject identified as being afflicted with an inflammatory metabolic disease.

Myocardial Ischemia and Ischemic Conditioning

The term "ischemic conditioning" as used herein refers to a technique in which tissue is rendered resistant to the deleterious effects of prolonged ischemia by exposure to brief episodes of stimulated ischemia, typically by pre-inducing brief ischemia/reperfusion cycles. Conditioning can be applied before (preconditioning), during (perconditioning), or after (postconditioning) the ischemic stressor. For the purposes of this description, all procedures describing a series of sub-lethal ischemic episodes are described using the general term "ischemic conditioning" whether it is done prior to, during, or after the ischemia as well as prior to, during, or after reperfusion.

In certain typical embodiments, ischemic conditioning may be performed mechanically by inducing brief, repeated periods of vascular occlusion. In human patients, this procedure may be produced by occlusion of an artery (coronary or remote, e.g. femoral) for brief periods of time followed by short periods of reperfusion as the occlusion is removed. The period of pre-exposure and the number of times the tissue is exposed to ischemia and reperfusion vary, the average typically being 3 to 5 minutes.

For example, mechanical conditioning (e.g. myocardial ischemic preconditioning, IPC) may be performed by occluding the coronary arteries e.g. left circumflex arteries for short periods, e.g. 2-5 minutes, 2-4 times prior to reperfusion, and/or post-conditioning may be performed for 1-2 minutes immediately after reperfusion. Remote ischemic preconditioning describes another version of this treatment, which includes applying a series of brief sub-lethal episodes of ischemia and reperfusion to an organ other than the target ischemic organ (such ischemic organ may be e.g. a heart). Applying a series of brief ischemic stimulae to a distant organ before, during, or after restoration of normal perfusion of the target ischemic organ is shown to activate protection from ischemia for the whole body and therefore reduces ischemia-reperfusion damage of the target organ. Over the years, a number of distant organs have been shown to provide cardioprotection in the setting of remote ischemic preconditioning including skeletal muscles on upper and lower extremities. Blood flow to the limb during the procedure is typically occluded for 3-5 min by a manually- or automatically-inflated blood pressure cuff or a tourniquet cuff. A deflation interval of 3-5 min then follows and this cycle is repeated 3-4 times.

In other embodiments, certain pharmacological agents have also been suggested to induce ischemic conditioning. Pharmacological conditioning may be induced e.g. by erythropoietin, opioid (e.g. morphine, sufentanil, remifentanil, methadone), insulin and an adenosine A1, A2A, A2B and/or A3 receptor agonist (e.g. adenosine, 5'-N-ethylcarboxamidoadenosine, N6-Cyclopentyladenosine, 2-(1-Hexynyl)-N-methyladenosine), as described (Nakano et al., 2000).

While these treatments have been shown to be effective in some patients, many patients have not demonstrated any clinical benefits from ischemic conditioning procedures. Notably, the procedure was found generally ineffective in elderly (over 65 years) and diabetic patients, which are of increased risk to develop coronary heart disease and are more likely to undergo cardiovascular and other surgical interventions (Nakano et al., 2000, Przyklenk, 2011). Surprisingly, ladostigil has been demonstrated herein to potentiate ischemic conditioning treatments even in these new patient populations.

Thus, according to some embodiments, the methods of the invention comprise administering ladostigil or a salt thereof to a subject in need thereof in combination (concomitantly or sequentially) with ischemic conditioning. In some embodiments, this combination treatment may be administered to a subject before surgical intervention e.g. cardiac surgery, e.g. in patients diagnosed with myocardial infarction, arrhythmias or heart failure.

According to one aspect, the invention provides a method of reducing or inhibiting ischemic injury (in particular, ischemic myocardial injury) in a subject in need thereof comprising administering to the subject ladostigil, thereby reducing or inhibiting ischemic injury in said subject. In various embodiments, the method may be used for reducing or inhibiting an ischemia-associated inflammation (e.g. myocardial post-ischemic inflammation), for reducing or inhibiting perioperative myocardial ischemic damage, for protecting against ischemic and/or reperfusion injury, for providing cardioprotection prior to, during, or following cardiac surgery or ischemic attack, and for enhancing the efficacy of ischemic conditioning in a subject in need thereof. In certain embodiments, said ladostigil is a daily dose of 10 to 60 mg ladostigil. In certain other embodiments, said ladostigil is ladostigil in an amount that inhibits no more than 25% or in other embodiments no more than 15% acetylcholinesterase activity, monoamine oxidase activity, or the combined activities of both enzymes. Each possibility represents a separate embodiment of the invention. Preferably, ladostigil is administered to said subject in combination with ischemic conditioning (e.g. prior to, concurrently with or after a conditioning treatment). For example, ladostigil may be chronically administered at a daily dose of 10-60 mg to said subject for two weeks prior to conditioning and may be continued after preconditioning, e.g. myocardial IPC performed by mechanical arterial occlusion to induce repeated cycles of brief ischemic episodes. Advantageously, the subject is an aged or diabetic subject, not otherwise amenable for ischemic conditioning. In a particular embodiment, said subject is over 65 years of age. In another particular embodiment, said subject is afflicted with diabetes, e.g. T2D. In another embodiment, the method comprises identifying said subject as a subject not amenable for myocardial ischemic conditioning.

In one embodiment, there is provided a method of protecting against reperfusion injury in a subject in need thereof comprising administering to the subject ladostigil or a salt thereof in combination with ischemic conditioning.

In another embodiment, there is provided a method of protecting against ischemic injury in a subject in need thereof comprising administering to the subject ladostigil or a salt thereof in combination with ischemic conditioning.

In another embodiment there is provided a method of providing cardioprotection prior to, during, or following cardiac surgery in a subject in need thereof comprising administering to the subject ladostigil or a salt thereof in combination with ischemic conditioning.

In another embodiment there is provided a method of providing cardioprotection prior to, during, or following ischemic attack in a selected from the group consisting of in need thereof administering to the subject ladostigil or a salt thereof in combination with ischemic conditioning.

In another embodiment, the invention provides a method for enhancing the efficacy of ischemic conditioning in a subject in need thereof, comprising administering to the subject ladostigil or a salt thereof (e.g. in concurrent or sequential combination with the ischemic conditioning).

In another aspect, there is provided a pharmaceutical composition comprising ladostigil or a pharmaceutically active salt thereof in combination with an ischemic conditioning therapy, selected from the group consisting of erythropoietin, an opioid (e.g. morphine, sufentanil, remifentanil, methadone), insulin and an adenosine A1, A2A, A2B and/or A3 receptor agonist (e.g. adenosine, 5'-N-ethylcarboxamidoadenosine, N6-Cyclopentyladenosine, 2-(1-Hexynyl)-N-methyladenosine). In a particular embodiment, the composition comprises 10 to 60 mg ladostigil in unit dosage form.

In another aspect there is provided a pharmaceutical pack, comprising ladostigil or a pharmaceutically active salt thereof and an ischemic conditioning therapy, selected from the group consisting of erythropoietin, an opioid (e.g. morphine, sufentanil, remifentanil, methadone), insulin and an adenosine A1, A2A, A2B and/or A3 receptor agonist (e.g. adenosine, 5'-N-ethylcarboxamidoadenosine, N6-Cyclopentyladenosine, 2-(1-Hexynyl)-N-methyladenosine). In a particular embodiment, the pharmaceutical pack comprises 10 to 60 mg ladostigil in unit dosage form.

Doses, formulations and administration routes for ischemic conditioning therapy drugs have been described, see, e.g., Nakano et al., 2000.

Gastrointestinal Inflammation and Inflammatory Diseases

Inflammatory bowel disease is a chronic inflammatory disorder of the gastrointestinal (GI) tract which has a multifactorial pathogenesis involving genetic, immune and environmental factors. The chronic inflammation in IBD results from dysregulation of the mucosal immune system and of the barrier function of the intestinal epithelium which results in strong macrophage infiltration into the intestinal tissues and the release of pro-inflammatory cytokines. A mouse model of UC induced by oral administration of dextran sodium sulphate (DSS) mimics the weight loss and diarrhea accompanied by blood and/or mucus seen in human subjects and also shows a reduction in colon length, crypt abnormalities, gastric dysmotility and infiltration of inflammatory cells.

Crohn's disease is characterized by ulcerations of the small and/or large intestines, but can affect the digestive system anywhere from the mouth to the anus. Various terms are used to describe Crohn's disease, and tend to reflect the portion of the gastrointestinal tract affected. For example, involvement of the large intestine (colon) only has been termed Crohn's colitis or granulomatous colitis, while involvement of the small intestine only has been termed Crohn's enteritis. Disease in the terminal portion of the small intestine, i.e. the ileum, has been termed Crohn's ileitis. When both the small intestine and the large intestine are involved, the condition has been termed Crohn's enterocolitis or ileocolitis. Ulcerative colitis is a condition related to Crohn's disease that involves only the colon, and collectively these diseases are frequently referred to as inflammatory bowel disease (IBD).

Irritable bowel syndrome (IBS) is a common disorder that has a pronounced effect on the quality of life and that accounts for a large proportion of healthcare costs. The disorder is characterized by lower abdominal pain, bloating, diarrhea, constipation, or constipation alternating with diarrhea. Altered bowel motility, visceral hyperalgesia, food allergy, bacterial overgrowth, psychosomatic factors, stress associated with the enteric nervous system have all been proposed as playing a part in the pathogenesis of IBS. Gastrointestinal inflammation may also be associated with irritable bowel syndrome, along with stress. Although the processes involved in the etiology and pathology of the disease are not fully elucidated, it has been reported that altered pro-inflammatory cytokine release may occur.

In another aspect, the invention provides a method of treating an inflammatory disease of the GI tract in a subject in need thereof, comprising administering to the subject ladostigil or a pharmaceutically active salt thereof, thereby treating the disease.

In another embodiment, the subject is identified as being afflicted with an inflammatory disease of the GI tract. In another embodiment, the method comprises identifying the subject as being afflicted with an inflammatory disease of the GI tract, and administering ladostigil or a pharmaceutically active salt thereof to said subject identified as being afflicted with an inflammatory disease of the GI tract.

In another preferable embodiment, the disease is a chronic inflammatory disease associated with pathological inflammation of the GI tract or a portion thereof in the individual that is persistent, whether continuous or intermittent.

In certain particular embodiments, the inflammatory gastrointestinal disease includes, but is not limited to, inflammatory bowel diseases (e.g. ulcerative colitis and Crohn's disease) irritable bowel syndrome, ileitis, chronic inflammatory intestinal disease, and celiac disease. Each possibility represents a separate embodiment of the present invention.

In another embodiment, the inflammatory disease is mediated by enhanced IL-6 levels (e.g. characterized by enhanced IL-6 blood levels).

According to another aspect, there is provided a method of inhibiting inflammation of the GI tract in a subject in need thereof, comprising administering to the subject ladostigil or a pharmaceutically active salt thereof, thereby inhibiting inflammation.

In another embodiment, the GI inflammation is associated with a chronic inflammatory disease of the gastrointestinal tract.

In another embodiment, the GI inflammation is associated with an autoimmune disease of the gastrointestinal tract.

In various embodiments, the compositions are particularly useful for treating chronic diseases associated with the gastrointestinal system including, but not limited to colitis, ileitis, Crohn's disease, chronic inflammatory intestinal disease, celiac disease, and inflammatory bowel disease.

In another particular embodiment, said disease is inflammatory bowel disease. In another particular embodiment, said disease is colitis. In another particular embodiment, said disease is Crohn's disease. In another particular embodiment, said disease is irritable bowel syndrome.

In another aspect, there is provided a method of inhibiting a clinical symptom associated with GI inflammation in a subject in need thereof, comprising administering to said subject, ladostigil or a pharmaceutically active salt thereof.

In certain embodiments, said ladostigil is a daily dose of 10 to 60 mg ladostigil. In certain other embodiments, said ladostigil is ladostigil in an amount that inhibits no more than 25% or in other embodiments no more than 15% acetylcholinesterase activity, monoamine oxidase activity, or the combined activities of both enzymes.

Doses and Means for Reducing Side Effects

According to certain embodiments, the methods of the invention are affected by administering to the subject a therapeutically effective dose of ladostigil or a salt thereof. A therapeutically effective amount as used herein refers to an amount sufficient to inhibit an inflammatory process in a subject in need thereof, and is thus useful for the treatment and amelioration of inflammatory diseases.

According to various embodiments, the invention contemplates the use of doses of 0.5 to 170 mg ladostigil. Preferably, a therapeutically effective dose is at least 10 mg ladostigil. In certain other preferred embodiments, a therapeutically effective dose is up to 150 or in other embodiments up to 120 or up to 100 mg ladostigil or a pharmaceutically active salt thereof (i.e. of the ladostigil base or an equivalent amount of the salt thereof). In another embodiment, a therapeutically effective amount is a daily dose of 10 to 100 mg ladostigil or a pharmaceutically active salt thereof. In another embodiment, a therapeutically effective amount is a daily dose of 10 to 80 mg ladostigil or a pharmaceutically active salt thereof. In another embodiment, a therapeutically effective amount is a daily dose of 10 to 60 mg ladostigil or a pharmaceutically active salt thereof. In another embodiment, a therapeutically effective amount is a daily dose of 10 to 50 mg ladostigil or a pharmaceutically active salt thereof. In another embodiment, a therapeutically effective amount is a daily dose of 10 to 40 mg ladostigil or a pharmaceutically active salt thereof.

In another embodiment, the cholinesterase (ChE) inhibitory activity of ladostigil is unrelated to its anti-inflammatory activity. In another embodiment, the unexpected pharmacokinetic profile of ladostigil indicates that administrating doses in the range of 10-60 mg ladostigil per day inhibits inflammation while reducing side effects associated with the inhibition of AChE and/or MAO activities. In another embodiment, the present invention provides that 10-120 preferably 10-100 mg ladostigil per day minimizes undesired inhibition of AChE and/or MAO activities by ladostigil therapy.

In another embodiment, minimizing undesired inhibition of AChE and/or MAO activities is equal to an inhibitory activity of up to (no more than) 40%. In another embodiment, minimizing undesired inhibition of AChE and/or MAO activities is equal to an inhibitory activity of up to 30%. In another embodiment, minimizing undesired inhibition of AChE and/or MAO activities is equal to an inhibitory activity of up to 25%. In another embodiment, minimizing undesired inhibition of AChE and/or MAO activities is equal to an inhibitory activity of up to 20%. In another embodiment, minimizing undesired inhibition of AChE and/or MAO activities is equal to an inhibitory activity of up to 18%. In another embodiment, minimizing undesired inhibition of AChE and/or MAO activities is equal to an inhibitory activity of up to 15%. In another embodiment, minimizing undesired inhibition of AChE and/or MAO activities is equal to an inhibitory activity of up to 10%. In another embodiment, minimizing undesired inhibition of AChE and/or MAO activities is equal to an inhibitory activity of up to 8%. In another embodiment, minimizing undesired inhibition of AChE and/or MAO activities is equal to an inhibitory activity of up to 5%.

The present invention surprisingly discloses that administering ladostigil at its maximal tolerable dose based on pharmacokinetics, previously considered clinically preferential, is not in fact advantageous and in some indications does not provide an enhanced anti-inflammatory therapeutic effect. Rather, it is unexpectedly disclosed herein, that dosages and formulations such as any of the aforementioned dosages and formulations disclosed by the invention provide clinically effective therapeutic effects with minimal side effects.

In another embodiment, a range of 10 to 60 mg ladostigil or a pharmaceutically active salt thereof per day ensures efficacy while minimizing side effects associated with the inhibition of AChE activity, MAO activity, or both. In another embodiment, a dose comprising from 10 to 40 mg ladostigil or a pharmaceutically active salt thereof ensures efficacy while minimizing side effects associated with the inhibition of AChE activity, MAO activity, or both. These doses provide up to 25% or 15% inhibition, respectively, of the above mentioned enzymes.

In another embodiment, the present invention provides that 10-120 mg ladostigil per day minimizes undesired inhibition of AChE activity, MAO activity, or their combination by ladostigil anti-inflammatory therapy. In another embodiment, the present invention provides that 10-80 mg ladostigil per day minimizes undesired inhibition of AChE activity, MAO activity, or their combination by ladostigil anti-inflammatory therapy. In another embodiment, the present invention provides that 10-40 mg ladostigil per day minimizes undesired inhibition of AChE activity, MAO activity, or their combination by ladostigil anti-inflammatory therapy. In another embodiment, the present invention provides that 40-120 mg ladostigil per day minimizes undesired inhibition of AChE activity, MAO activity, or their combination by ladostigil anti-inflammatory therapy. In another embodiment, the present invention provides that 20-60 mg ladostigil per day minimizes undesired inhibition of AChE activity, MAO activity, or their combination by ladostigil anti-inflammatory therapy. In another embodiment, the phrase "anti-inflammatory therapy" includes systemic anti-inflammatory therapy, septic shock therapy, or therapy for any disease associated with inflammation and systemic or acute inflammation.

In another embodiment, minimizing side effects associated with the inhibition of cholinesterase activity by ladostigil is utilizing low doses that essentially fail to inhibit cholinesterase activity. In another embodiment, inhibiting inflammation with ladostigil further comprises: (1) minimizing side effects associated with the inhibition of MAO activity; or (2) utilizing low doses that fail to inhibit MAO activity.

In another embodiment, minimizing side effects associated with the inhibition of AChE is minimizing the risk of SLUDGE syndrome. In another embodiment, side effects include but are not limited to: anorexia, nausea, vomiting, diarrhea, insomnia, bradycardia, hypotension, hypersecretion, bronchoconstriction, GI tract hypermotility, muscle contraction. In another embodiment, minimizing is abolishing. In another embodiment, minimizing is reducing the risk of any side effect or a combination of side effects within a treated population by at least 10%, 20%, 40%, 50%, 60%, 75%, 80%, or 90%. In another embodiment, minimizing is reducing the frequency of any side effect or a combination of side effects in a patient by at least 10%, 20%, 40%, 50%, 60%, 75%, 80%, or 90%.

In another embodiment, ladostigil and its pharmaceutically acceptable salts, when administered in the dosages and formulations disclosed herein provide unexpectedly minimal undesired side effect with good safety and efficacy profiles. In another embodiment, efficacy as used herein relates to ladostigil's anti-inflammatory activity. In another embodiment, efficacy as used herein relates to ladostigil's systemic anti-inflammatory activity. In another embodiment, ladostigil and its pharmaceutically acceptable salts are administered in multiple doses or as a single dose. In either case, the amount of drug released and available for absorption ensure that side effects are minimized, while exposing the subject to sufficient drug to provide a clinically beneficial effect.

In another embodiment, the present invention provides that the phrase "daily dose" is the total dose of ladostigil or a salt thereof per day (24 hours). In another embodiment, the present invention provides that a "daily dose" is administered in one dose or once a day. In another embodiment, the present invention provides that a "daily dose" is administered in two doses or twice a day. In another embodiment, the present invention provides that a "daily dose" is divided into two doses. In another embodiment, the present invention provides that a dose is administered every 6, 7, 8, 9, 10, 11, or 12 hours.

In another embodiment, ladostigil or a pharmaceutical salt thereof is/are formulated for immediate release. In another embodiment, ladostigil or a pharmaceutical salt thereof is/are formulated for sustained release.

In another embodiment, the present invention is directed to the use of ladostigil or a pharmaceutical salt thereof in the preparation of a medicament for inhibiting inflammation, wherein the use is selected from the group consisting of: total daily administration of 10 to 60 mg ladostigil or a pharmaceutical salt thereof once a day. In some embodiments, ladostigil or a pharmaceutically active salt thereof is administered in two equal divided doses per day.

In another embodiment, the present invention unexpectedly provides ladostigil in the range of 10-80 mg per day that minimizes or even abolishes side effects associated with the inhibition of MAO and/or AChE activity. In another embodiment, the present invention unexpectedly provides ladostigil in the range of 10-80 mg per day that minimizes or even refractory with respect to the actual inhibition of MAO and/or AChE activity. In another embodiment, the present invention unexpectedly provides ladostigil in the range of 10-60 mg per day that minimizes or even abolishes side effects associated with the inhibition of MAO and/or AChE activity. In another embodiment, the present invention unexpectedly provides ladostigil in the range of 10-60 mg per day that minimizes or even refractory with respect to the actual inhibition of MAO and/or AChE activity. In another embodiment, the present invention unexpectedly provides ladostigil in the range of 10-40 mg per day that minimizes or even abolishes side effects associated with the inhibition of MAO and/or AChE activity. In another embodiment, the present invention unexpectedly provides ladostigil in the range of 10-40 mg per day that minimizes or even refractory with respect to the actual inhibition of MAO and/or AChE activity. In another embodiment, the present invention unexpectedly provides ladostigil in the range of 10-30 mg per day that minimizes or even abolishes side effects associated with the inhibition of MAO and/or AChE activity. In another embodiment, the present invention unexpectedly provides ladostigil in the range of 10-30 mg per day that minimizes or even refractory with respect to the actual inhibition of MAO and/or AChE activity. In another embodiment, the present invention provides a method for inhibiting inflammation: (a) while minimizing side effects associated with the inhibition of cholinesterase activity and/or (b) without inhibiting MAO and AChE in a subject in need thereof, comprising administering to the subject 10 to 100 mg ladostigil or a pharmaceutically active per day. In another embodiment, the present invention provides a method for inhibiting inflammation: (a) while minimizing side effects associated with the inhibition of cholinesterase activity and/or (b) without inhibiting MAO and AChE in a subject in need thereof, comprising administering to the subject 10 to 100 mg ladostigil or a pharmaceutically active per day for at least 4 days. In another embodiment, the present invention provides a method for inhibiting inflammation: (a) while minimizing side effects associated with the inhibition of cholinesterase activity and/or (b) without inhibiting MAO and AChE in a subject in need thereof, comprising administering to the subject 10 to 40 mg ladostigil or a pharmaceutically active per day for at least 4 days. In another embodiment, the present invention provides a method for inhibiting inflammation: (a) while minimizing side effects associated with the inhibition of cholinesterase activity and/or (b) without inhibiting MAO and AChE in a subject in need thereof, comprising administering to the subject 30 to 80 mg ladostigil or a pharmaceutically active per day for at least 4 days.

In another embodiment, the exact time period of "at least 4 days" includes determination of reduced side effects associated with AChE inhibition and/or MAO inhibition. In another embodiment, at least 4 days is at least 7 days. In another embodiment, at least 4 days is 7 days. In another embodiment, at least 4 days is 8 days. In another embodiment, at least 4 days is 9 days. In another embodiment, at least 4 days is 18 days. In another embodiment, gradual increase in the dose of ladostigil or a pharmaceutically active salt thereof, in time periods of at least 7 days, maintains the efficacy of the drug while minimizing side effects associated with AChE inhibition. In another embodiment, gradual increase in the dose of ladostigil or a pharmaceutically active salt thereof, in time periods of 7 days, maintains the efficacy of the drug while minimizing side effects associated with AChE inhibition. In another embodiment, the time period is designed for each patient individually according to blood measures as described herein and/or side effects associated with AChE inhibition as described herein.

In another embodiment, administering ladostigil or a pharmaceutically active salt thereof twice a day is administering equal doses of ladostigil or a pharmaceutically active salt thereof twice a day. In another embodiment, there is at least 6 hours gap between each dose. In another embodiment, there is at least 8 hours gap between each dose. In another embodiment, there is at least 10 hours gap between each dose. In another embodiment, there is at least 12 hours gap between each dose.

In another embodiment, the first dose is administered during the morning hours. In another embodiment, the first dose, the second dose or both is/are administered prior to eating and/or drinking. In another embodiment, the first dose is administered prior to eating and/or drinking in the morning hours. In another embodiment, the first dose is administered at least 15 minutes prior to eating and/or drinking in the morning hours. In another embodiment, the first dose, the second dose or both is/are administered at least 15 minutes prior to eating and/or drinking. In another embodiment, the first dose, the second dose or both is/are administered at least 30 minutes prior to eating and/or drinking. In another embodiment, the first dose, second dose or both is/are administered at least 45 minutes prior to eating and/or drinking. In another embodiment, the first dose, second dose or both is/are administered at least 60 minutes prior to eating and/or drinking. In another embodiment, the first dose, second dose or both is/are administered at least 75 minutes prior to eating and/or drinking. In another embodiment, the first dose, second dose or both is/are administered at least 90 minutes prior to eating and/or drinking. In another embodiment, daily administering is administering within 24 hours. In another embodiment, daily administering is administering from awakening to two hours before bedtime.

In another embodiment, administering ladostigil or a pharmaceutically active salt thereof twice a day is administering ladostigil or a pharmaceutically active salt thereof in a first dose and a second dose. In another embodiment, the first dose comprises equal or less amount of ladostigil or a pharmaceutically active salt thereof than the second dose.

In another embodiment, twice a day includes a first dose and a second dose. In another embodiment, a first dose is administered in the morning hours. In another embodiment, a second dose is administered in the evening hours. In another embodiment, a second dose is administered 3-6 hours before bed time. In another embodiment, a second dose is administered before 20:00, 19:00, or 18:00. In another embodiment, both the first dose and the second dose are administered prior to eating and/or drinking as provided herein. In another embodiment, the first dose is administered upon awakening and the second dose is administered 3-6 hours before bed time. In another embodiment, the first dose is administered at least 6 hours before the second dose. In another embodiment, the first dose is administered at least 7 hours before the second dose. In another embodiment, the first dose is administered at least 8 hours before the second dose. In another embodiment, the first dose is administered at least 5-8 hours before the second dose.

In another embodiment, administration as described herein is chronic administration. As used herein, the term "chronic administration" refers to repeated administration of pharmaceutical compositions comprising a specific amount of active ingredient for at least 12 days, at least 16 days, at least 21 days, or four continuous weeks. Preferably such administration is repeated for at least 12 weeks or more, 24 weeks or more or 52 weeks or more.

In another embodiment, the term "ladostigil" includes pharmaceutically active salts, hydrates and solvates thereof.

Pharmaceutically active salt of ladostigil may include for example hydrochloride, sulfate, tartrate, maleate, citrate, phosphate, acetate, lactate, fumarate, hydrobromide, mesylate, pamoate, hydroiodide, nitrate, and methylsulfate, tosylate. In some embodiments, ladostigil is provided as ladostigil hemitartrate (also referred to herein as ladostigil tartrate).

Another embodiment, Ladostigil metabolites include: 1) (R)-HCPAI; 2) (R)-MCPAI; 3) (R)-ECPAI; 4) (R)-CAI; 5) (R)-HPAI; 6) (R)-MCAI and 7) (R)-ECAI. In another embodiment, a metabolite of the invention is formed through the actions of CYP 450 isoenzymes in the liver, with the exception of (R)-HPAI, which is the result of ladostigil hydrolysis by AChE. In another embodiment, the metabolites listed above inhibit AChE at different concentrations with the exception of (R)-HPAI which does not inhibit AChE but is a potent inhibitor of MAO activity. In some embodiments, dosages and formulations such as any of the aforementioned dosages and formulations are prepared with release profile such that the maximum concentration of ladostigil's metabolites (R)-MCPAI and (R)-MCAI in blood plasma does not exceed 400 ng/ml and 80 ng/ml respectively. According to certain particular embodiments, the range of concentration of (R)-MCPAI in blood plasma lies between 50-250 ng/ml. In other embodiments, the concentration of (R)-MCPAI in blood plasma is up to 100 or 250 ng/ml and is at least 50, 100 or 150 ng/ml. In a particular embodiment, the concentration of (R)-MCPAI in blood plasma is about 120 ng/ml. According to certain other particular embodiments, the maximum concentration of (R)-MCAI in blood plasma does not exceed 10, 20 or 30 ng/ml. In other embodiments, the concentration of (R)-MCAI in blood plasma is at least 3 ng/ml. In a particular embodiment, the concentration of (R)-MCAI in blood plasma is about 10-30 ng/ml.

Pharmaceutical Compositions

Pharmaceutical compositions may be administered by any route that provides the safe, clinically effective amounts of ladostigil or pharmaceutically acceptable salts thereof. In some embodiments, the drug is provided by oral or rectal administration.

In another embodiment, the pharmaceutical composition is an oral immediate release composition. In another embodiment, the term "immediate release" pharmaceutical formulation includes any formulation in which the rate of release of ladostigil or a pharmaceutically acceptable salt thereof from the formulation and/or the absorption of drug, is neither appreciably, nor intentionally, retarded by galenic manipulations. In the present case, immediate release may be provided for by way of an appropriate pharmaceutically acceptable diluent or carrier, which diluent or carrier does not prolong, to an appreciable extent, the rate of drug release and/or absorption. In another embodiment, the term excludes formulations which are adapted to provide for "modified", "controlled", "sustained", "prolonged", "extended" or "delayed" release of ladostigil or a pharmaceutically acceptable salt thereof.

Pharmaceutical compositions that comprise ladostigil or pharmaceutically active salts thereof and pharmaceutically acceptable carriers or diluents are provided. The pharmaceutical compositions may be formulated by one having ordinary skill in the art. Suitable pharmaceutical carriers are described in Remington's Pharmaceutical Sciences, A. Osol, a standard reference text in this field, which is incorporated herein by reference.

Unit dosage forms comprise the active ingredient ladostigil or a pharmaceutically active salt thereof ladostigil and pharmaceutically excipients or carriers such as fillers, disintegrants, lubricants, glidants, and soluble and insoluble polymers.

Examples of fillers include water-soluble compressible carbohydrates such as sugars (e.g., dextrose, sucrose, maltose, and lactose); sugar-alcohols (e.g., mannitol, sorbitol, malitol, xylitol); starch hydrolysates (e.g., dextrins, maltodextrins, and the like); water insoluble plastically deforming materials (e.g., microcrystalline cellulose or other cellulosic derivatives); and water-insoluble brittle fracture materials (e.g., dicalcium phosphate, tricalcium phosphate and the like and mixtures thereof).

Examples of binders include dry binders such as polyvinyl pyrrolidone, hydroxypropylmethylcellulose, and the like; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, starches, and the like; and derivatives and mixtures thereof.

Examples of disintegrants for making a core or core portion by compression include sodium starch glycolate, cross-linked polyvinylpyrrolidone, cross-linked carboxymethylcellulose, starches, microcrystalline cellulose, and the like.

Examples of lubricants for making a core or core portion by compression include long chain fatty acids and their salts, such as magnesium stearate and stearic acid, talc, glycerides and waxes.

Examples of glidants for making a core or core portion by compression include colloidal silicon dioxide, and the like.

Examples of polymers include hydrophilic polymers and materials, insoluble polymers and materials, pH-dependent polymers, and the like. Hydrophilic materials include: water swellable cellulose derivatives, polyalkalene glycols, thermoplastic polyalkalene oxides, acrylic polymers, hydrocolloids, clays, gelling starches, and swelling cross-linked polymers, and derivatives, copolymers, and combinations thereof. Examples of cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, hydroxypropylethylcellulose. Examples of polyalkalene glycols include polyethylene glycol. Examples of thermoplastic polyalkalene oxides include poly (ethylene oxide). Examples of acrylic polymers include potassium methacrylatedivinylbenzene copolymer, polymethylmethacrylate, CARBOPOL (high-molecular weight cross-linked acrylic acid homopolymers and copolymers), and the like. Examples of hydrocolloids include alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan. Examples of clays include smectites such as bentonite, kaolin, and laponite; magnesium trisilicate, magnesium aluminum silicate, and the like, and derivatives and mixtures thereof. Examples of gelling starches include acid hydrolyzed starches, swelling starches such as sodium starch glycolate, and derivatives thereof. Examples of cross-linked polymers include cross-linked polyvinyl pyrrolidone, cross-linked agar, and cross-linked carboxymethylcellose sodium.

Examples of insoluble materials include water-insoluble polymers, and low-melting hydrophobic materials. Examples of water-insoluble polymers include ethylcellulose, polyvinyl alcohols, polyvinyl acetate, polycaprolactones, cellulose acetate and its derivatives, acrylates, methacrylates, acrylic acid copolymers; and the like and derivatives, copolymers, and combinations thereof. Examples of low-melting hydrophobic materials include fats, fatty acid esters, phospholipids, and waxes. Examples of fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides. Examples of phospholipids include phosphatidyl choline, phosphatidyl serine, phosphatidyl inositol, and phosphatidic acid. Examples of suitable waxes include carnauba wax, spermaceti wax, beeswax, candelilla wax, shellac wax, microcrystalline wax, and paraffin wax; fat-containing mixtures such as chocolate; and the like.

pH-dependent polymers include enteric cellulose derivatives, for example hydroxypropyl methylcellulose phthalate, hydroxypropyl methylcellulose acetate succinate, cellulose acetate phthalate; natural resins such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, and poly(methacrylic acid, methyl methacrylate) 1:1, and the like, and derivatives, salts, copolymers, and combinations thereof.

Other excipients may include preservatives; sweeteners such as aspartame, acesulfame potassium, sucralose, and saccharin; flavorants; colorants; antioxidants; surfactants; wetting agents; and the like and mixtures thereof. Dosage unit forms may be coated with polishes and the like.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.933% of ladostigil or a salt thereof, or in another embodiment, from about 0.01% to about 10%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, the compositions comprise from about 0.001% to about 10.0% w/v of ladostigil or a salt thereof, more preferably from about 00.1% to about 2.0, which is used for systemic delivery of ladostigil or a salt thereof by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables of the invention are formulated in aqueous solutions. In one embodiment, injectables of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulphate and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredients to allow for the preparation of highly concentrated solutions.

In some embodiments, the present invention herein demonstrates that ladostigil provides an enhanced anti-inflammatory effect that is sufficient for effective use in the absence of other anti-inflammatory agents. Thus, according to some embodiments, the methods of the invention contemplate the use of ladostigil as a sole active ingredient.

Yet, in other embodiments, the invention relates to the use of ladostigil in combination with other drugs, and in particular provides combination compositions and kits comprising ladostigil and a drug useful for promoting or potentiating myocardial protection, as detailed herein. Thus, provided herein are pharmaceutical compositions and packs comprising ladostigil and one or more additional active ingredients selected from the group consisting of erythropoietin, an opioid (e.g. morphine, sufentanil, remifentanil, methadone), insulin and an adenosine A1, A2A, A2B and/or A3 receptor agonist (e.g. adenosine, 5'-N-ethylcarboxamidoadenosine, N6-Cyclopentyladenosine, 2-(1-Hexynyl)-N-methyladenosine). Each possibility represents a separate embodiment of the invention. According to particular embodiments, the invention provides a pharmaceutical composition wherein the active ingredients consist of a first active ingredient being ladostigil or a salt thereof (e.g. ladostigil tartrate), and a second active ingredient selected from the group consisting of: erythropoietin, morphine, sufentanil, remifentanil, methadone, insulin, adenosine, 5'-N-ethylcarboxamidoadenosine, N6-Cyclopentyladenosine and 2-(1-Hexynyl)-N-methyladenosine. Each possibility represents a separate embodiment of the invention.

In a particular embodiment, the composition or pharmaceutical pack comprises 10 to 60 mg ladostigil in unit dosage form. In other particular embodiments, effective doses of the additional active ingredients are known in the art and may be adjusted to the patient by the skilled artisan. In another particular embodiment, the composition is formulated for oral administration using e.g. excipients as specified above. In other embodiments, the invention relates to compositions, or to pharmaceutical packs or kits wherein one component or more may be formulated for another administration route, e.g. for i.v. injection. For example, without limitation, recombinant erythropoietin is marketed under the brand names Epogen® or Procrit® in an isotonic sodium chloride/sodium citrate buffered solution or a sodium chloride/sodium phosphate buffered solution for intravenous (i.v.) or subcutaneous (s.c.) administration. Various products are marketed with 10,000-40,000 Units/mL. Morphine is available at various brands for a variety of administration routes, including oral solid dosage forms (e.g. Avinza, Kadian, MS Contin) and parenteral dosage forms e.g. for i.v., s.c. or i.m. injection (e.g. Morphine Sulfate Injections at 0.5-15 mg/ml). Insulin is available e.g. as solutions for parenteral injections, e.g. at 100 units/mL under the brand names Novolog and Humulin. Adenosine is available e.g. under the brand names Adenocard and Adenoscan for i.v. injection or infusion at 3 mg/mL.

The following examples are presented in order to more fully illustrate some embodiments of the invention. They should, in no way be construed, however, as limiting the broad scope of the invention.

EXAMPLES

The examples described herein present experimental results in various animal models examining the effects of ladostigil hemitartrate (ladostigil tartrate). Therefore, the term "ladostigil" as it appears in the following examples refers to ladostigil tartrate.

Example 1

Experimental Colitis and Gastrointestinal Inflammation

Acute Colitis Induced by DSS in Mice

BALB/c OlaHsd male mice aged 8-9 weeks and weighing 25-30 g were purchased from Harlan (Jerusalem, Israel) and housed in standard cages of up to 5 per cage in the pathogen free Animal Facility of the Institute for Drug Research. All experiments were performed in accordance with the Principles of Laboratory Animal Care (NIH publication #85-23, revised 1985) protocols MD-09-12197-4. Acute colitis was induced in mice by administration of 5% DSS solution (M.Wt.=36,000–50, MP Biomedicals, LLC, Solon, Ohio, USA) in water for 8 days. The DSS solution was freshly prepared every day. Mice were provided with food and water or DSS solution ad libitum during the experiment. They were divided into groups of 10 as follows: Vehicle control group: mice drank water and were given water (1 ml/100 gm) once daily by gavage for 8 days; Drug control group: mice drank water and were given ladostigil (10 mg/kg) by gavage once daily for 8 days. DSS untreated group: mice drank 5% DSS for 7 days and water on the 8th day and were given water (1 ml/100 g) once daily by gavage for 8 days. Drug treated group: mice drank 5% DSS followed by water as above and were given ladostigil (5 or 10 mg/kg) by gavage once daily for 8 days. The volume of 5% DSS solution consumed was measured for each group of mice and the average volume/mouse was calculated. On the eighth day, the mice were anesthetized by $CO_2$ and sacrificed by cervical dislocation 2 h after the last dose of ladostigil. Samples of colon and spleen were taken for measurement of cytokines MPO, cytokines and ChE activity.

Evaluation of Clinical Signs of Acute Colitis in Mice

Body weight, stool consistency and the presence of blood in the stools was recorded daily for each mouse. These data were used to calculate a disease activity index (DAI) as described by Kullmann et al, (2001). The score ranged between 0-4 for all three parameters and was composed as follows: Weight loss: none=0, 1-5%=1, 5-10%=2, 10-20%=3, >20%=4. Percent of weight loss on days 7 and 8 relative to the first day was calculated for all the groups. Stool evaluation: normal pellets=0, loose stools which do not stick to the anus=2, diarrhea=4. Bleeding: none=0, hemoccult=2, gross bleeding=4. The maximum DAI score was 4 based on a combination of scores of weight loss (relative to that on the first day of the experiment), stool consistency and bleeding, divided by 3. After sacrifice the length of the colon segment from the cecum to the rectum was measured.

Cytokine Detection in Colon

TNF-α, IL-6, and IL-1β levels in homogenized colon were measured by means of a BioLegend ELISA Mouse kit. One cm of colon was homogenized in ice-cold PBS buffer containing protease inhibitor cocktail (Sigma, St. Louis, Mo., USA; dilution 1:100) using a Polytron homogenizer, and then centrifuged for 15 min at 14,000 rpm at 4° C. Supernatants were diluted 1:5 in diluent buffer supplied in the kit and applied to 96-well MaxiSorb Elisa plates according to manufacturer's protocol. Total protein concentration in the tissue supernatant was measured by means of a BCA kit. Levels of cytokines are expressed as pg/mg total tissue protein.

Determination of Cholinesterase Activity in Spleen and Colon

In experiments on the effect of chronic treatment with ladostigil on ChE activity in mice drinking DSS, the spleen was rapidly removed as described above, together with a colon segment of about 0.5 cm in length taken from the proximal area. Spleen and colon segments were washed in cold phosphate buffered saline (PBS) before they were frozen at −80° C. For assay, the tissue was unfrozen and weighed and PBS was added to each tissue at a ratio of 1 mg tissue to 1 ml. Tissues were homogenized at a speed of 24,000 rpm in cold phosphate buffer pH 7 containing 0.1% Triton and centrifuged at 14000 rpm. Aliquots of plasma and the supernatant from the spleen and colon were incubated with acetylthiocholine and dinitro benzoic acid in phosphate buffer pH 7 and the rate of development of the yellow color was measured as described by Ellman et al, (1961). Percent inhibition of ChE activity was calculated by comparison with that of control mice given water by gavage. Protein concentration was determined by means of by Pierce BCA Protein Assay Kit (Thermo Scientific, USA) according to the manufacturer's instructions. It is noted, that ChE activity in the colon and spleen of mice is attributed mainly to that of AChE while that in mouse plasma is mainly attributable to BuChE.

Neutrophil Infiltration in Colonic Tissues of Mice

Neutrophil infiltration was monitored by measuring myeloperoxidase (MPO) activity in colon segments according to the protocol described by Bradley (1982) in 96-well micro-titer plates by mixing 10 μl of the supernatant with 290 μl of o-dianisidine dihydrochloride solution. Data were interpolated from a MPO standard curve. MPO activity was expressed as units per μg total protein measured in the sample by Pierce BCA Protein Assay Kit as described above.

Effect of Ladostigil Treatment on Macroscopic Markers of Colitis in Mice

Figure 2:
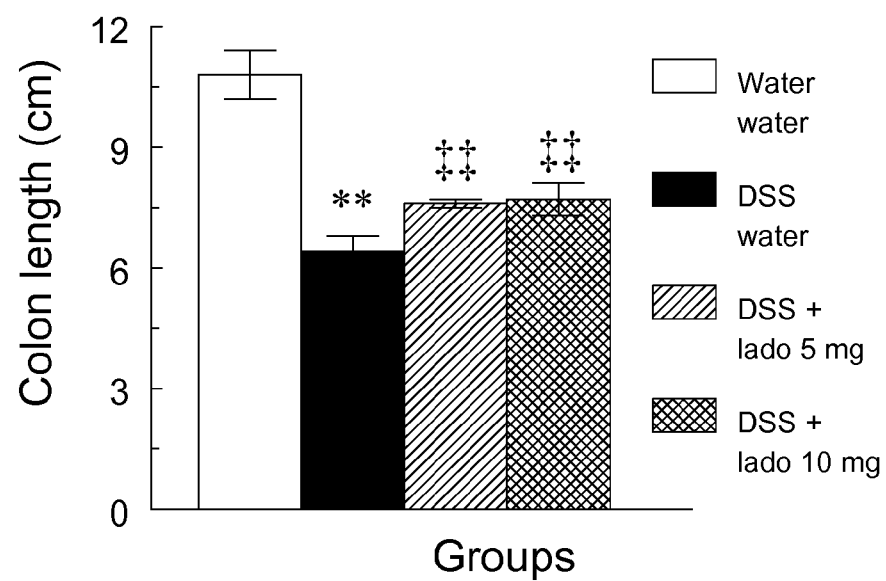
FIG. 2 demonstrates the effect of ladostigil on colon shrinkage induced in mice by DSS solution.

The body weight of mice receiving ladostigil (5 or 10 mg/kg), like those given water by gavage increased by 2-3% during 8 days, in contrast to those given rivastigmine (1 mg/kg/day) in which body weight decreased by 4.7%. Neither dose of ladostigil caused any significant inhibition of ChE in the colon, while rivastigmine inhibited colonic ChE by >60% (Table 1). Mice drinking 5% DSS showed a weight loss of 15% (FIG. 1, top left panel), which was reduced by both doses of ladostigil by almost 50%. Rivastigmine did not prevent the weight loss induced by DSS. Diarrhea with occult blood was the earliest clinical sign of acute colitis and appeared on the 5th day. On days 7 and 8 of DSS treatment, signs of colitis were more severe and included loose stools or diarrhea, blood in feces resulting in almost maximal scores in all untreated mice on day 8. Diarrhea was significantly decreased by both doses of ladostigil on day 7, and bleeding, by ladostigil (5 mg/kg), on day 8 (FIG. 1, top right panel). Disease activity index (DAI) calculated for the drug treated groups was significantly different from that of the group drinking DSS given water (p<0.01) on days 7 and 8 (FIG. 1, bottom right panel). Macroscopic examination in mice given water by gavage and drinking 5% DSS solution revealed a significant decrease of >30% in colon length and signs of hyperemia and inflammation which was significantly less in those treated with ladostigil (5 and 10 mg/kg) (FIG. 2).

Cytokine secretion and myeloperoxidase activity (an indicator of colonic lymphocyte infiltration) confirmed a potent anti-inflammatory activity of ladostigil in the colon of DSS-treated mice. Measurements were made on the $8^{th}$ day of DSS ingestion when TNF-α levels are no longer elevated significantly. The lower dose of ladostigil, 5 mg/kg was more effective than 10 mg/kg in reducing levels of IL-1β and MPO activity than ladostigil 10 mg/kg.

TABLE 1

Effect of DSS (5%) and ladostigil treatment on cholinesterase activity in the spleen and colon and myeloperoxidase activity in the colon of mice

| Treatment | ChE activity colon[a] | ChE activity spleen[a] |
|---|---|---|
| Water-water | 20.6 ± 1.6 | 17.6 ± 1.1 |
| DSS-water | 18.2 ± 1.2 | 12.2 ± 1.5* |
| DSS- lado 5 mg/kg | 18.5 ± 1.4 | 10.8 ± 0.6 |
| DSS- lado 10 mg/kg | 16.7 ± 1.2 | 10.2 ± 0.7 |

Lado = ladostigil. ChE = cholinesterase. Ladostigil was given orally once daily.
[a]Cholinesterase activity expressed as μmoles of acetylthiocholine hydrolyzed/min/mg protein and includes both AChE and BuChE. Significantly different from water-water *p < 0.05 In FIGS. 1-3, black columns represent mice treated with DSS plus water; hatched columns represent mice treated with DSS and ladostigil (5 mg/kg); cross-hatched columns represent mice treated with DSS and ladostigil (10 mg/kg), and white columns represent healthy mice not treated with DSS (receiving water injections).

FIG. 1. Depicts the effect of ladostigil on macroscopic parameters of colitis on days 7 and 8 of treatment with 5% DSS. DAI=disease activity index. Significantly different from DSS-water, * p<0.05; ** p<0.001.

FIG. 2. Depicts the effect of ladostigil on colon shrinkage induced in mice by DSS solution. Significantly different from water-water, ** p<0.001; significantly different from DSS-water, ‡‡ p<0.01.

Figure 3:
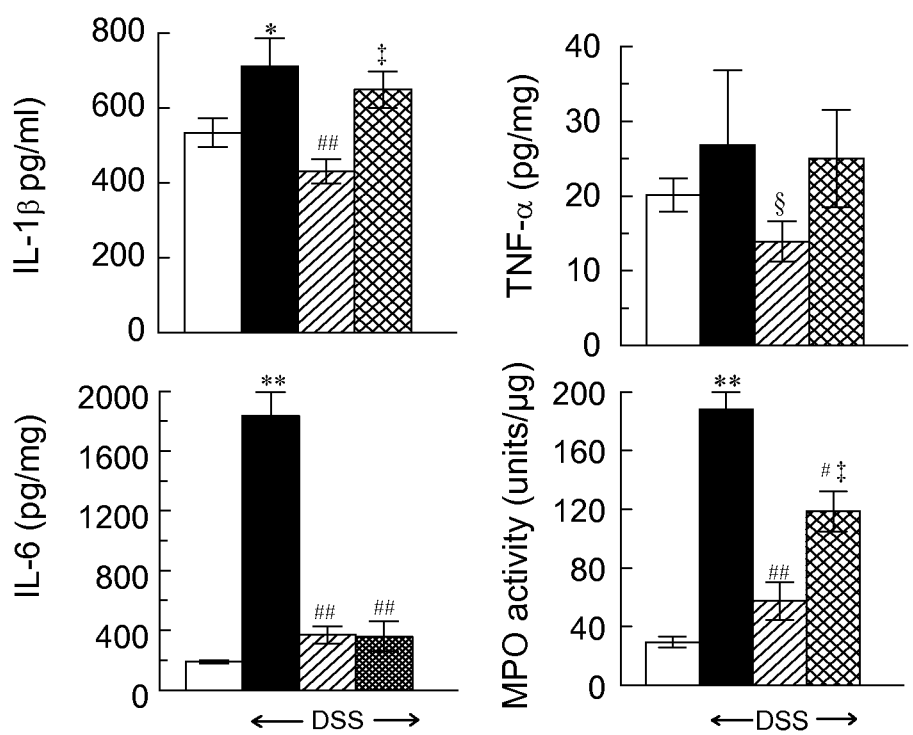
FIG. 3 illustrates the effect of ladostigil on increase in cytokines and myeloperoxidase in mice with DSS-induced colitis.

FIG. 3. Depicts the effect of ladostigil on increase in cytokines and myeloperoxidase in mice with DSS-induced colitis. MPO=myeloperoxidase. Significantly different from water-water * p<0.05; ** p<0.01; Significantly different from DSS-water, § p<0.07; # p<0.05; ## p<0.01; significantly different from DSS-lado (5 mg/kg), ‡ p<0.05.

Example 2

Myocardial Ischemic Preconditioning

Methods

Four groups of male rats of the Wistar strain were used for these studies; a) 3-months old untreated; b) 22 months old, untreated; c) 22 months old treated from the age of 16 months by daily oral administration of ladostigil hemitartrate at a dose of 1 mg/kg/day (hereinafter "low dose"; d) 22 months old treated from the age of 16 months by daily oral administration of ladostigil hemitartrate at a dose of 8.5 mg/kg/day (hereinafter "high dose"). Only the latter dose was shown to inhibit MAO-A after chronic treatment in rats.

On the day of the experiment, rats were injected with i.p. sodium heparin (500 units/kg) followed 30 min later by 80 mg/kg ketamine plus 5 mg/kg xylazine i.p. Bilateral thoracotomy was performed and hearts with a segment of the ascending aorta were rapidly excised, put in ice-cold heparinized saline and mounted onto the Langendorff apparatus. They were perfused with a modified Krebs-Henseleit (KH) buffer as described in Chevion et al. (1993). Heart rate (HR), developed pressure (DP), and its derivatives (+dp/dt and −dp/dt) were recorded. All primary data were processed using a customized version of LabView 7.1 software (National Instruments, Austin, Tex., USA). Work index (WI=Heart Rate×DP) was used as an indicator of heart contractility. The degree of cardio-protection was expressed by the percent (ratio) of two values: WI at the completion of the experiment (at the 120th min) and WI at the completion of the stabilization phase (at the 10th min).

Experimental protocol: Three basic experimental protocols were employed: (i) continuous (un-interrupted) perfusion: (ii) stabilization (25 min) followed by ischemia and reperfusion (35/60 min) (I/R), and (iii) stabilization (10 min) followed by IPC, ischemia and reperfusion (IPC+I/R). The hemodynamic parameters of the heart were monitored and recorded continuously throughout, during all experimental protocols. Under the I/R protocol, the stabilization phase was extended from 10 to 25 min to compensate for the 15 min of the IPC procedure, which consisted of 3 cycles of (2 min ischemia and 3 min perfusion).

Results

The 'work index' (WI) values after 60 min reperfusion were 27% and 28%, respectively for young and aged rats, as compared to their corresponding baseline values at the completion of the stabilization phase (Table 2). After IPC, the hearts of young rats were more tolerant to ischemia, and the WI increased to 73% of young control but that of old rats did not increase and tended to be slightly lower than without IPC. Treatment of aging rats with ladostigil at either dose had no significant effect on WI after 60 min ischemia and reperfusion. However, after IPC, the WI of hearts from rats given ladostigil (1 mg/kg/day) was increased to >50% which did not differ significantly from that of young rats. In rats given 8.5 mg/kg/day the increase in WI was much smaller.

TABLE 2

Potentiation of Myocardial Ischemic Preconditioning by Ladostigil

| Age | Protocol | Treatment | n = | HR | DP | WI |
|---|---|---|---|---|---|---|
| Young | I/R | No treatment | 6 | 87 ± 13 | 29 ± 14 | 27 ± 15 |
| Old | I/R | No treatment | 5 | 101 ± 33 | 31 ± 19 | 28 ± 11 |
| Old | I/R | Low dose | 3 | 67 ± 15 | 20 ± 10 | 13 ± 6 |
| Old | I/R | High dose | 4 | 83 ± 8 | 14 ± 6 | 12 ± 5 |
| Young | IPC + I/R | No treatment | 7 | 97 ± 17 | 77 ± 13 | 73 ± 11 |
| Old | IPC + I/R | No treatment | 4 | 76 ± 6 | 31 ± 14 | 23 ± 11 |
| Old | IPC + I/R | Low dose | 6 | 77 ± 8 | 68 ± 15 | 53 ± 12 |
| Old | IPC + I/R | High dose | 5 | 92 ± 28 | 30 ± 12 | 26 ± 6 |
| Old | I/R vs IPC + I/R Low dose (ladostigil) | | p | 0.013524 | 0.007295 | 0.00425 |
| Old | I/R vs IPC + I/R high dose (ladostigil) | | | 0.547862 | 0.048827 | 0.008782 |
| Old | IPC + I/R | Lado vs NO-Treatment | | 0.668495 | 0.003552 | 0.004055 |

"I/R vs IPC + I/R" presents the statistical significance (p value) for difference for treatment with each dose before and after ischemic preconditioning (I/R).
"IPC + I/R Lado vs NO-Treatment" presents the statistical significance (p value) of Ladostigil treatment with low dose (1 mg/kg) and I/R compared to untreated old rats.

No significant ChE inhibition in the heart or brain was detected in rats treated with ladostigil at 1 mg/kg/day. In rats treated with ladostigil at 8.5 mg/kg/day, MAO-A activity in the heart was inhibited by 50-60%, and ChE activity was inhibited by 30%. Thus, ladostigil was able to potentiate IPC treatment in aged rats without any significant inhibition of ChE and MAO, while the dose that was high enough to inhibit these enzymes was even found to be inactive.

Example 3

Diabetes

Male *Psammomys obesus* gerbils aged 3.5-4 months were given a high-energy diet consisting of 938.5 g/Kg version of 2018SC+F Harlan Tekled Ltd., USA, supplemented with soybean oil to a final fat concentration of 6%. After one week on the diet, blood was taken for measurement of glucose and ChE activity. Half of the animals were given ladostigil (17 mg/kg/day) by gavage while the remainder received tap water by the same route. Blood was taken from the tail once weekly for measurement of glucose as described in Kalman R., et al, (2001). Lab Anim. 35:346-352. After three weeks of treatment the animals they were deeply anesthetized, blood was taken by cardiac puncture for measurement of ChE activity, glucose and insulin levels and the pancreas removed for section and staining with haematoxylin and eosin and the number of islets counted. Initial and final glucose and insulin levels are shown in the Table 3. Blood glucose of 11 animals had reached values exceeding 200 mg/dL after one week on the high energy diet and the average value for the whole group was 300±27 mg/dL. The degree of ChE inhibition produced by ladostigil in plasma taken three hours after the last gavage was determined by comparison for the control BuChE activity taken from the same gerbil before treatment by the method of Ellman (1961) and was found to be 50±3%. It is noted, that cholinesterase activity in plasma of *Psammomys obesus* is mostly mediated by butyrylcholinesterase (BuChE) rather than by AChE. Since ladostigil is at least ten times more potent in inhibiting BuChE than in inhibiting AChE, a human dose equivalent to that used in these experiments would exert much less AChE inhibition.

Figure 4A:
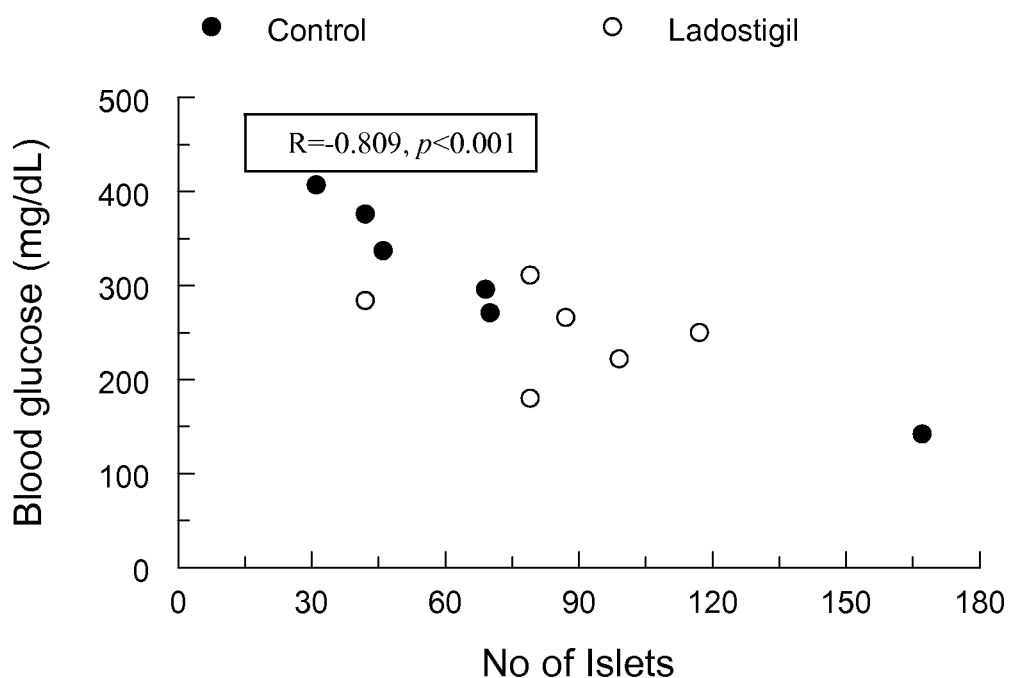
FIGS. 4A-4B depict the relation of blood glucose level to that of insulin and the number of pancreatic islet cells.
Figure 4B:
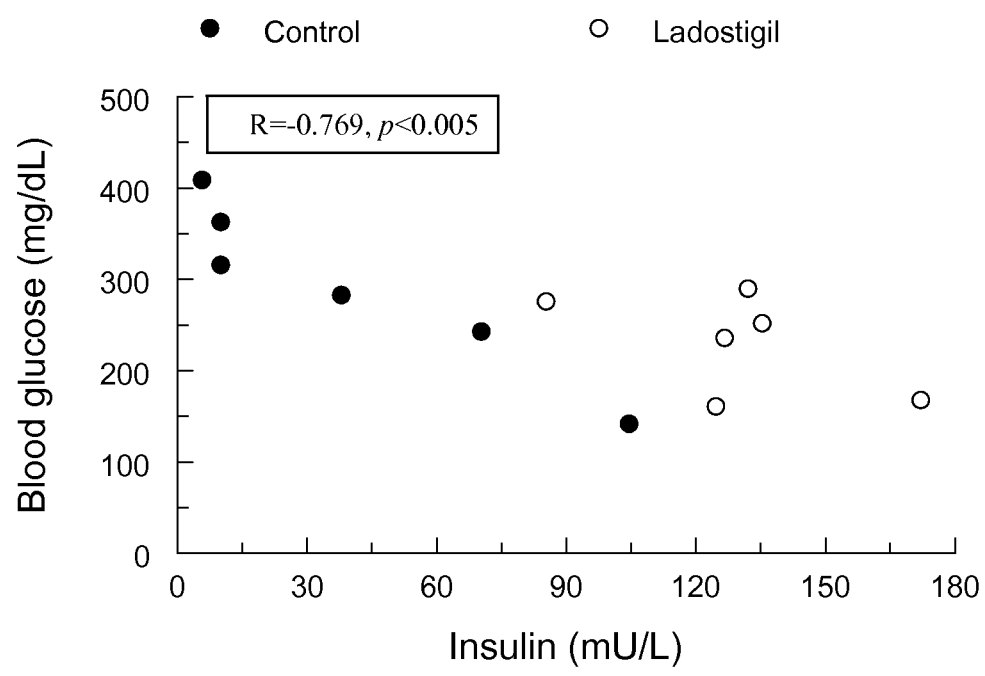

With one exception, blood glucose levels increased further during the next three weeks in all untreated gerbils. Ladostigil treatment resulted in a decrease in blood glucose levels in all six animals. In the ladostigil-treated gerbils the higher plasma level of insulin was associated with a larger number of intact pancreatic islet cells. A highly significant correlation was found between the plasma levels of glucose and those of insulin, and between plasma levels of glucose and the number of pancreatic islet cells (FIG. 4).

The data show that treatment of gerbils with ladostigil (17 mg/kg/day) after they have already developed diabetes can protect the islet cells and enable them to maintain adequate levels of insulin to lower blood glucose.

TABLE 3

Effect of ladostigil treatment and high energy diet on plasma glucose and insulin levels and number of pancreatic islet cells in gerbils.

| | Before | After 3 weeks of treatment | | | | |
|---|---|---|---|---|---|---|
| Group | treatment Glucose (mg/dL) | Glucose (mg/dL) | Change in glucose | Insulin (mU/L) | No of islets | Phase |
| Controls | 383 | 407 | +24 | 5.7 | 31 | D |
| | 307 | 337 | +30 | 10 | 46 | D |
| | 334 | 376 | +42 | 10 | 42 | D |
| | 393 | 296 | −97 | 37.9 | 69 | D |
| | 263 | 271 | +8 | 70.3 | 70 | C |
| | 99 | 143 | +44 | 104.5 | 167 | B |
| Ladostigil 17 mg/kg | 420 | 284 | −136 | 132 | 42 | C |
| | 273 | 250 | −23 | 126.6 | 117 | C |
| | 200 | 180 | −20 | 124.6 | 79 | C |
| | 352 | 311 | −41 | 85.3 | 79 | C |
| | 287 | 222 | −65 | 172 | 99 | C |
| | 285 | 266 | −19 | 135.3 | 87 | C |

Example 4

Systemic Anti-inflammatory Activity of Ladostigil: Response to Endotoxin

Evaluation of Anti-inflammatory Effect of Ladostigil in Spleen of Mice Injected with LPS Male Balb/c mice (aged 6-7 weeks, weighing 25-30 gm) were given ladostigil 10 mg/kg by gavage or 1 ml/kg saline followed 15 min later by an intra-peritoneal (i.p.) injection of LPS (10 mg/kg). For measurement of cytokine levels in the spleen and blood the mice were sacrificed 4 h after drug administration, blood collected in heparinized tubes and centrifuged to obtain plasma and the spleen was rapidly removed and weighed. Plasma and spleen were frozen in liquid nitrogen and stored at −80° C. until use.

For measurement of cytokine levels the tissue was diluted in PBS containing 0.8% NaCl, 0.144% NaHPO$_4$, 0.024% KH$_2$PO$_4$ and protease inhibitor cocktail (Sigma Israel, P8340) and homogenized in an Ultra-TURRAX® homogenizer at a speed of 24,000 rpm, centrifuged at 14000 g for 15 min at 4° C. Cytokines were detected in the supernatant by using ELISA kits for cytokines IL-1β, IL-6, and TNF-α (Biolegend) following the manufacturer's protocol. Each experiment was performed 4 times with 6 replicate measures in each experiment. Protein concentration in each sample was determined with Bradford reagent (Bio-RAD, 500-0006).

Determination of Cholinesterase Activity in Spleen and Plasma

Ladostigil 10 mg/kg or saline 1 mg/kg were given by gavage to groups of 6 Balb-C male mice weighing 24-30 gm. The mice were sacrificed 120 min later when ChE inhibition reaches its peak. The spleen was rapidly removed and weighed and blood was centrifuged at 14000 rpm at room temperature for 4 min to provide plasma. Phosphate buffer was added to the spleen at a ratio of 1 mg/ml and the tissue was homogenized at a speed of 24,000 rpm in cold phosphate buffer pH=7 containing 0.1% Triton and centrifuged at 14000 rpm. Aliquots of plasma and the supernatant from the spleen were incubated with acetylthiocholine and dinitro benzoic acid in phosphate buffer pH 7 and the rate of development of the yellow color was measured as described by Ellman et al, (1961). Percent inhibition of ChE activity was calculated by comparison with that of control mice given with saline. Protein concentration was determined by means of Bradford reagent (Bio-RAD, 500-0006) and results represented as activity/mg protein.

Results

Four hours after an i.p. injection of LPS (10 mg/kg) there was a considerable increase in the levels of TNF-α, IL-1β and IL-6 in the supernatant prepared from the spleen (Table 4). Ladostigil caused a significant reduction in the levels of cytokines induced in the spleen by LPS (p<0.01). TNF-α levels were reduced by 49.6%, IL-1β levels by 28.1% and those of IL-6 by 46.7%.

There was no significant inhibition of ChE either in spleen 7.8±6.4% (SD) or in plasma 5.7±2.1% (SD) two hours after oral administration of ladostigil in mice.

In conclusion, ladostigil given orally to mice at a dose that does not cause any significant inhibition (up to about 10% inhibition) of ChE in the spleen or plasma, prior to injection of LPS reduced by 28-50% the elevation of pro-inflammatory cytokines in the spleen which are associated with systemic inflammation, acute inflammation, and septic shock.

TABLE 4

Effect of ladostigil on increase in cytokine in spleen four hours after injection of LPS

| Treatment | TNF-α pg/mg protein | IL-1β ng/mg protein | IL-6 pg/mg protein |
|---|---|---|---|
| Saline | ND | 0.38 ± 0.02 | ND |
| Saline + LPS 10 mg/kg | 15.7 ± 0.4 | 1.91 ± 0.12 | 350 ± 23 |
| Ladostigil 10 mg/kg + LPS 10 mg/kg | 8.3 ± 0.9* | 1.37 ± 0.04* | 179 ± 20* |

Data represent the mean value ± SEM. ND = non detectable. Significantly different from saline + LPS
*p < 0.01.

Example 5

Response to Endotoxin—Comparison to Rivastigmine

Evaluation of Anti-inflammatory Effect of Ladostigil in Spleen of Mice Injected with LPS Male Balb/c mice (aged 8-9 weeks, weighing 25-30 gm) were given ladostigil (10 or 20 mg/kg) or rivastigmine (0.5 or 1 mg/kg) by gavage, or water (1 ml/100 g), followed 15 min later by an intra-peritoneal injection of LPS (10 mg/kg). Control mice were given LPS and water by gavage (1 ml/100 g). For measurement of cytokine levels in the spleen and blood the mice were sacrificed 4 h after drug administration, blood collected in heparinized tubes and centrifuged to obtain plasma and the spleen was rapidly removed and weighed. Plasma and spleen were frozen in liquid nitrogen and stored at −80° C. until use. For measurement of cytokine levels, the tissue was diluted in PBS containing 0.8% NaCl, 0.144% NaHPO$_4$, 0.024% KH$_2$PO$_4$ and protease inhibitor cocktail (Sigma Israel, P8340) and homogenized in an Ultra-TURRAX® homogenizer at a speed of 24,000 rpm, centrifuged at 14000 g for 15 min at 4° C. Cytokines were detected in the supernatant by using ELISA kits for cytokines IL-1β, IL-6, and TNF-α (Biolegend) following the manufacturer's protocol. Each experiment was performed twice with 8 replicate measures in each experiment. Protein concentration in each sample was determined with Bradford reagent (Bio-RAD, 500-0006).

Determination of Cholinesterase Activity

For the LPS experiment involving a single administration, ladostigil (10 or 20 mg/kg) in a volume of 1 ml/100 g or water (1 ml/100 g) were given by gavage to groups of 6-8 Balb-C male mice weighing 24-30 g and LPS as described above. The mice were sacrificed 120 min later when ChE inhibition reaches its peak. Blood was taken into heparinized tubes and centrifuged at 14000 rpm at room temperature for 4 min to provide plasma and the spleen was rapidly removed, weighed, frozen in liquid nitrogen and stored at −80° C. until assayed. It is noted, that ChE inhibition in mouse plasma is mainly attributed to BuChE activity, and in mouse spleen—mainly to AChE activity.

Percent inhibition of ChE activity was calculated by comparison with that of control mice given water by gavage as described in Example 1 above.

Results—Anti-inflammatory Effect of Ladostigil in Spleen of Mice Injected with LPS Four h after injection of LPS (10 mg/kg) there was a considerable increase in the levels of TNF-α, IL-1β and IL-6 in the supernatant prepared from the spleen (Table 5). Ladostigil treatment (10 mg/kg) reduced levels of TNF-α by 49.7±7.6%, IL-1β, by 31.1±4.3 and IL-6, by 50.0±7.2 (Table 5). Ladostigil (20 mg/kg) caused a significant reduction of 42.7±8.3% in the levels of IL-6 but had no effect on those of TNF-α or IL-1β. Rivastigmine (0.5 mg/kg) had no effect on levels of any of the three cytokines. Rivastigmine (1 mg/kg) significantly reduced IL-1β and IL-6, but not of TNF-α in the spleen (Table 5).

TABLE 5

Effect of ladostigil on cytokine levels in spleen four hours after injection of LPS (10 mg/kg)

| Treatment | TNF-α (pg/mg) | IL-1β (pg/mg) | IL-6 (pg/mg) |
|---|---|---|---|
| Saline | 2.5 ± 0.3 | 84 ± 7 | 6.29 ± 2.85 |
| Saline + LPS (10 mg/kg) | 19.1 ± 1.2 | 636 ± 52 | 701 ± 43 |
| Ladostigil (10 mg/kg) + LPS | 9.6 ± 1.5** | 401 ± 40* | 351 ± 50** |
| Ladostigil (20 mg/kg) + LPS | 17.1 ± 1.9 | 591 ± 17 | 454 ± 59* |
| Rivastigmine (0.5 mg/kg) + LPS | 16.8 ± 2.5 | 551 ± 31 | 569 ± 89 |
| Rivastigmine (1 mg/kg) + LPS | 16.5 ± 2.2 | 440 ± 40* | 462 ± 66* |

Data represent the mean value ± SEM. Significantly different from saline + LPS
*p < 0.05,
**p < 0.01

The effect of a single dose of ladostigil (10 or 20 mg/kg) on ChE activity in mouse plasma and spleen, 120 min after oral administration (time of peak inhibition in spleen) is shown in Table 6. Ladostigil (10 mg/kg) did not significantly inhibit ChE activity in plasma or in the spleen, while a dose of 20 mg/kg, inhibited ChE in plasma by 27.4±5.9% and in the spleen by 36.9±1.5%. The inhibition of ChE by rivastigmine (0.5 mg/kg) 60 min after oral administration (time of peak inhibition) in plasma and spleen was similar to that produced by ladostigil (20 mg/kg), while rivastigmine (1 mg/kg) inhibited the enzyme by about twice as much. These data demonstrate that ChE inhibition is not a prerequisite for the anti-inflammatory effect of ladostigil and may even interfere with it. On the other hand, rivastigmine did not reduce the level of inflammatory cytokines in the spleen unless it inhibited ChE by more than 50% indicating that the two drugs act by independent mechanisms.

TABLE 6

Inhibition of ChE (%) in plasma and spleen after acute administration of ladostigil or rivastigmine in LPS injected mice.

| Treatment | Plasma | Spleen |
|---|---|---|
| Ladostigil 10 (mg/kg) | 7.8 ± 2.4 | 15.1 ± 3.6 |
| Ladostigil 20 (mg/kg) | 27.4 ± 5.9* | 28.1 ± 1.9** |
| Rivastigmine 0.5 mg/kg | 28 ± 4.5* | 32.6 ± 5.6** |
| Rivastigmine 1 mg/kg | 56.8 ± 6.1** | 65.8 ± 3.2** |

[a] ChE inhibition relative to value in appropriate saline control injected with LPS. Significantly different from saline,
*$p < 0.05$,
**$p < 0.01$.

REFERENCES

Borovikova, L. V. et al. 2000. Nature 405 458-462.
Cha J. et al. Ann Thorac Surg. 2008 May; 85(5):1678-85.
Chevion M. et al. Proc Natl Acad Sci USA 1993; 90:1102-6.
Holmes et al. Neurology. 2009 Sep. 8; 73(10):768-74.
Kullmann et al, 2001. Int J Colorectal Dis 16: 238-246.
Langley et al., 2004. J. Neuroimmunol. 148(1-2):140-5.
Nakano et al., Pharmacol Ther 2000; 86:263-75.
Nizri E, et al., 2005. Neurosci Lett. 376(1):46-50.
Nizri E, et al., 2006. Neuropharmacology 50(5):540-7.
Nizri, E., et al. 2007. International Immunopharmacology. 7, 1129-1139.
Panarsky et al., J Neuroimmune Pharmacol. 2012 June; 7(2):488-98.
Panarsky et al. Alzheimer's & Dementia: The Journal of the Alzheimer's Association. Vol. 6, Issue 4, Supplement, Pages S557-S558, July 2010.
Przyklenk K. Drugs Aging 2011; 28:331-43.
Reale, M. et al., 2004. J. Neuroimmunol.; 148:162-171.
Sandborn, W. J., et al. 1997. A randomized, double-blind, placebo-controlled trial. *Ann. Intern. Med.* 126:364-371.
Tyagi E et al., 2007. Life Sci.; 80:1977-1983.
Wang, H H. et al., 2004. Nat. Med. 10:1216-1221.
Wellen K. E., et al., (2005). J. Clin. Invest 115: 1111-1119.

What is claimed is:

1. A method for treating an inflammorory metabolic disease in a subject in need thereof, the method comprising administering a dail dose of 10 to 60 mg ladostigil or a pharmaceutically active salt thereof to a subject, thereby treating the disease in the subject, wherein the disease is selected from the group consisting of type 2 diabetes mellitus, type 1 diabetes mellitus, pre-diabetes, dyslipidemia, and insulin resistance, and the subject does not suffer from Alzheimer's disease or dementia, wherein said ladostigil is administered in an amount that inhibits no more than 15% acetylcholinesterase activity, monoamine oxidase activity, or the combined activities of both enzymes.

2. The method of claim 1, wherein said ladostigil or said pharmaceutically active salt thereof is formulated in an oral dosage form or in a rectal dosage form.

3. The method of claim 1, wherein said administered ladostigil or pharmaceutically active salt thereof is ladostigil tartrate and/or is ladostigil as a sole active ingredient.

4. The method of claim 1, wherein said disease is type 2 diabetes mellitus.

* * * * *